United States Patent
Baldwin

(10) Patent No.: US 11,857,304 B1
(45) Date of Patent: Jan. 2, 2024

(54) RADIO FREQUENCY ANTENNA WITH VARYING IMPEDANCE FOR WEARABLE

(71) Applicant: AMAZON TECHNOLOGIES, INC., Seattle, WA (US)

(72) Inventor: Leo Benedict Baldwin, Seattle, WA (US)

(73) Assignee: AMAZON TECHNOLOGIES, INC., Seattle, WA (US)

( * ) Notice: Subject to any disclaimer, the term of this patent is extended or adjusted under 35 U.S.C. 154(b) by 1162 days.

(21) Appl. No.: 16/450,703

(22) Filed: Jun. 24, 2019

(51) Int. Cl.
*A61B 5/05* (2021.01)
*A61B 5/145* (2006.01)
*A61B 5/1495* (2006.01)
*A61B 5/00* (2006.01)
*A61B 5/0507* (2021.01)
*H01Q 1/27* (2006.01)

(52) U.S. Cl.
CPC .............. *A61B 5/05* (2013.01); *A61B 5/0507* (2013.01); *A61B 5/1495* (2013.01); *A61B 5/14532* (2013.01); *A61B 5/14546* (2013.01); *A61B 5/681* (2013.01); *H01Q 1/273* (2013.01)

(58) Field of Classification Search
CPC ..... A61B 5/05; A61B 5/0507; A61B 5/14532; A61B 5/14546; A61B 5/1495; A61B 5/681; H01Q 1/273
See application file for complete search history.

(56) References Cited

U.S. PATENT DOCUMENTS

2020/0187793 A1\* 6/2020 Leabman ............. A61B 5/0507

\* cited by examiner

*Primary Examiner* — Eric F Winakur
*Assistant Examiner* — Abid A Mustansir
(74) *Attorney, Agent, or Firm* — Lindauer Law, PLLC

(57) ABSTRACT

Data about concentration of one or more types of molecules present within a human body are determined noninvasively using radio frequency signals. These signals generated at very low power levels are emitted and acquired using an antenna mounted to a wearable device. Information about changes to the signals is indicative of the concentration of one or more types of molecules within the user. The antenna includes two or more elements with a varying distance between them which reduces or eliminates power reflection and improves overall efficiency. The varying distance provides a first impedance at terminals of the antenna and a second impedance elsewhere on the antenna, such as midway along a long axis of the antenna. The first impedance matches an impedance of a transmitter output, a receiver input, or both. The second impedance results in the signal extending away from the antenna towards the user.

20 Claims, 8 Drawing Sheets

RADIO FREQUENCY ANTENNA WITH VARYING IMPEDANCE FOR WEARABLE

BACKGROUND

Physiological data may be used to help a user manage their health, make more informed decisions, and improve the quality of their life. For example, physiological data such as hydration level, glucose concentration, and so forth may be useful for health management.

BRIEF DESCRIPTION OF FIGURES

The detailed description is set forth with reference to the accompanying figures. In the figures, the left-most digit(s) of a reference number identifies the figure in which the reference number first appears. The use of the same reference numbers in different figures indicates similar or identical items or features.

Figure 1:
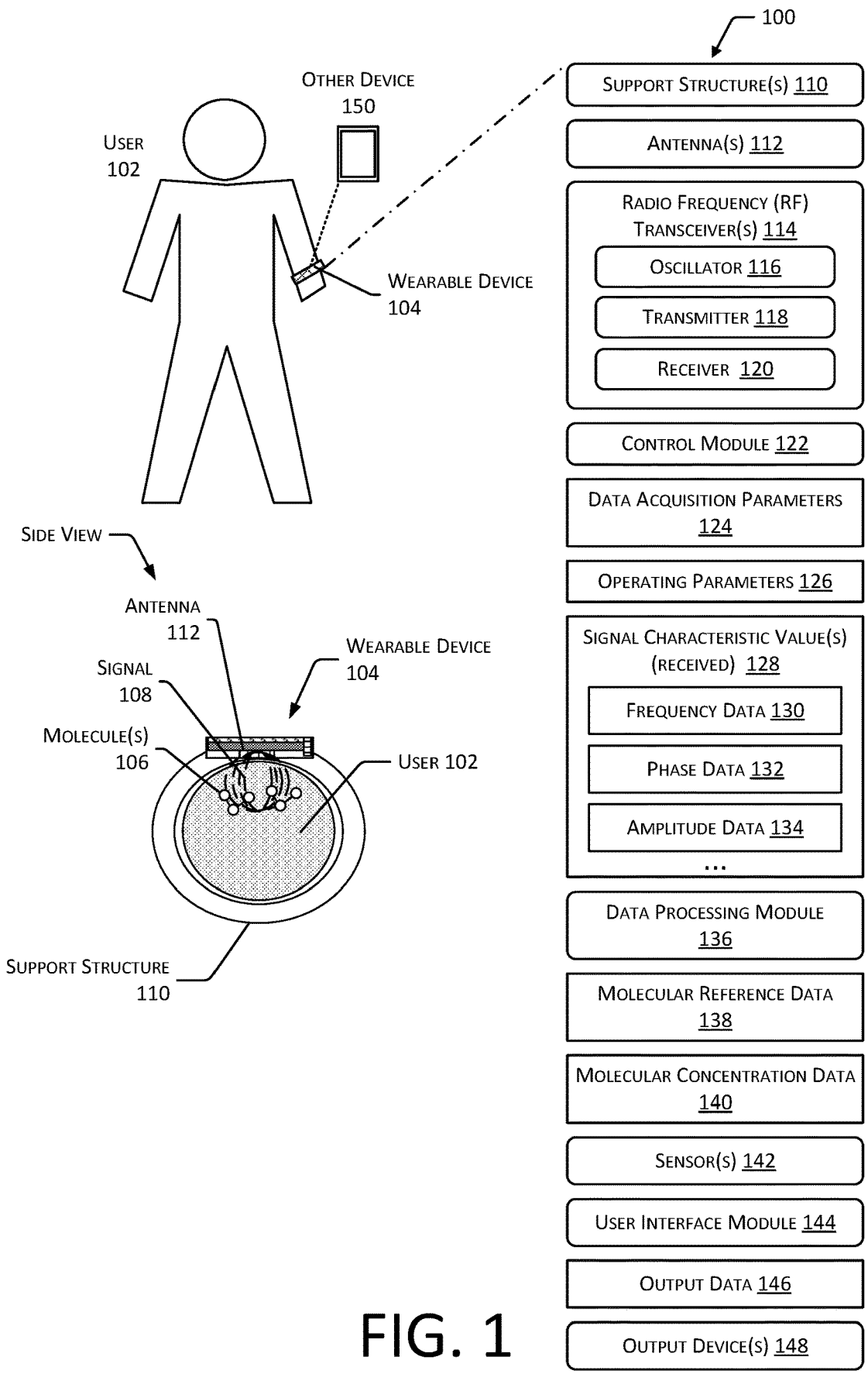
FIG. 1 is an illustrative system that includes a wearable device with an antenna that uses radio frequency signals to determine molecular concentrations of molecules of interest in the user, according to one implementation.

While implementations are described herein by way of example, those skilled in the art will recognize that the implementations are not limited to the examples or figures described. It should be understood that the figures and detailed description thereto are not intended to limit implementations to the particular form disclosed but, on the contrary, the intention is to cover all modifications, equivalents, and alternatives falling within the spirit and scope as defined by the appended claims. The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include," "including," and "includes" mean including, but not limited to.

DETAILED DESCRIPTION

The human body utilizes many different kinds of molecules to function. For example, glucose provides energy for cellular activity while water provides a medium to carry molecules such as glucose and also acts as a reactant. Other molecules may be introduced into the body. For example, alcohol may be consumed, carbon monoxide may be inhaled, a pesticide may be absorbed through the skin, and so forth.

Information about the concentration of one or more types of molecules within the tissues of the body is useful in many situations. For example, a person who is diabetic needs to know the concentration of glucose in their blood in order to keep that concentration in a healthy range. In another example, an athlete needs to make sure they are sufficiently hydrated to maximize their physical performance and avoid injury due to dehydration. Continuing the example, the athlete may also want to monitor their sodium and potassium levels to maintain an optimal level of electrolytes.

Traditionally information about the concentration of one or more types of molecules has been obtained through invasive measurement of a sample obtained from the person. For example, to measure glucose levels a sample of blood is taken and applied to a chemical test strip. In another example, a rough estimate of dehydration can be obtained by assessing skin turgor, such as by pinching the skin on the back of the hand. However, traditional methods have significant drawbacks. Obtaining samples of blood or other tissues within the body requires piercing the skin, injuring the person and introducing a possibility of infection. Additionally, such testing can be costly due to special handling considerations, use of consumables such as reagents, and so forth. Mechanical measurements, such as assessment of skin turgor, lack precision.

Described in this disclosure is an antenna that facilitates non-invasively measuring molecular concentration of one or more types of molecules within a user. The antenna is used to emit and acquire radio frequency (RF) signals. The presence or concentration of types of molecules change the characteristics of the emitted signal. These changes may then be used to determine the presence or concentration of the types of molecules.

Measuring the molecular concentration of the one or more types of molecules is facilitated by acquiring information about signals that penetrate beyond the surface of the skin to some sample depth. For example, the sample depth may describe a useful distance into the user with which the signal is able to penetrate and produce usable data. The sample depth may be determined based on the radiated power of the RF signal, efficiency of the antenna, power of the signal being acquired, sensitivity of the receiver, and so forth. A particular sample depth may be used to assess types of molecules of interest. For example, for assessing the concentrations of molecules expected to be present in interstitial fluids between cells, such as glucose, a sample depth of between 5 mm and 10 mm may provide useful information.

Impedance in an electronic circuit measures the opposition of that circuit to the flow of current when a voltage is applied. Circuits that involve RF signals have a given impedance at a given frequency.

A match in the impedance of a source to a load results in an efficient transfer of signal power. For example, a transmitter may have an output impedance of 50 ohms at 1 GHz. If the transmitter output is connected to a load, such as an antenna, which has a matching impedance of 50 ohms at 1 GHz, the power produced by the transmitter is transferred to the antenna with greatest efficiency. Similarly, a receiver with an input impedance of 50 ohms connected to the same antenna will transfer an acquired signal to the receiver with greatest efficiency.

A mismatch in the impedance of the source to the load can produce a variety of undesirable effects. A mismatch results in a loss of power transferred between the source and the load. In another example, the transmitter output with an output impedance of 50 ohms at 1 GHz is connected to an antenna with a mismatching impedance of 100 ohms at 1

GHz. Due to this mismatch, only a portion of the power produced by the transmitter is transferred to the antenna, decreasing the overall efficiency of the system. The power which is not transferred to the antenna may be reflected back to the transmitter output. As a result, less energy ultimately is emitted by the antenna and the transmitter may be damaged. Similarly, a mismatch between the antenna and the receiver input decreases the power of the acquired signal that is transferred to the receiver. As a result, the strength of the received signal is decreased.

Traditionally, impedance mismatches may be either avoided by engineering the circuitry to exhibit substantially the same impedance, or by using an impedance matching network. However, such engineering results in antennas which do not provide the necessary signal penetration to provide a useful sample depth. Furthermore, such engineering may result in antenna designs which are not suitable for use in a wearable device where the available volume for an antenna is constrained. For example, such antenna designs may require too much volume to be practicable for a wearable device.

Impedance matching networks comprise circuitry that operate to transform one impedance to another. However, impedance matching networks introduce additional signal losses, also require volume within a wearable device, increase overall system complexity, and increase cost.

The antennas described in this disclosure present, at a first portion, a first impedance which facilitates power transfer to devices connected to the first portion, such as a transmitter or receiver. Within the antennas, a second portion presents a second impedance due to a change in the geometry of the antenna elements. The transition from the first impedance to the second impedance is gradual, reducing or eliminating reflected power. This maximizes the transfer of power of a signal to be emitted as well as power of a signal to be acquired. The second portion of the antenna produces an electric field which extends farther away from the antenna, to the desired sample depth. A particular sample depth may be selected by selecting a particular geometry.

The antennas may comprise several elements arranged with variable spacing between the elements. In one implementation, the antenna may comprise a first element and a second element that are separated from one another by a distance of five millimeters (mm) at a first end of the first section, gradually widen out to be separated by a distance of fifteen mm at a midpoint of the second section, and then narrow back to a five mm distance at a second end.

The changes in distance also increase fringing effects, resulting in the electric field associated with the antenna extending farther from the antenna and toward the user. This increases the sample depth to which a transmitted signal penetrates and from which a receive signal may be detected.

The change in distance between the elements is gradual in that the elements may curve or slow towards or away from one another, avoiding discontinuities or transitions in the structure of the elements that would introduce an abrupt change in impedance at the frequency or frequencies that the antenna will be used for.

The antennas described in this disclosure are very low profile, having a minimum overall height, allowing them to be readily incorporated into a wearable device. By providing a desired impedance in the first section, no matching network is necessary improving overall efficiency while reducing size, complexity, and cost. The antennas are relatively broadband, allowing operation on various different frequencies. The antennas are also durable and relatively inexpensive to manufacture. Arrays of antennas may also be used. For example, multiple antennas may be used to increase the volume of the user sampled.

During operation of the system, a radio frequency transmitter generates a first signal that is emitted from one or more antenna elements of the antenna. The same antenna or another antenna may be used to acquire the first signal, which is detected using a radio frequency receiver. One or more signal characteristic values are determined. For example, the signal characteristic values may be indicative of a frequency of the received signal, a phase difference between the signal as transmitted and the signal as received, amplitude of the received signal, and so forth. Signals may be transmitted and received in different frequency bands, providing signal characteristic values for the different bands. For example, a first signal may be transmitted at 5 GHz, a second signal at 10 GHz, a third signal at 50 GHz, a fourth signal at 100 GHz, and so forth.

The signal characteristic values may be compared to molecular reference data to determine one or more of presence of or concentration of one or more types of molecules present within the user. In one implementation, the phase differences at different frequencies may be used to determine a concentration of a type of molecule, such as glucose. For example, the molecular concentration data may describe a linear relationship between phase differences at particular frequencies and glucose concentration. In other implementations, the concentration of other types of molecules may be determined. For example, the concentration of water may be determined, providing information about a hydration level of the user.

Overall exposure to radio frequency (RF) signals is limited, as the output power is extremely low and duration of the radio frequency (RF) signals may be very short. For example, the modulation of the signals may be a continuous wave with a total duration of less than 1 millisecond (ms) and with a transmitter output power of 0 decibel-milliwatts (dBm). The sampling frequency, that is how often the RF signals are transmitted to gather data, may also be low, further reducing RF exposure. For example, the system may transmit signals once every six minutes, producing sets of ten samples per hour with each set comprising signal characteristic data for the various frequency bands.

By using the system with the antenna and techniques described in this disclosure, information about the concentration of various types of molecules at the sample depth within the user may be determined non-invasively.

The information provided by the system may be used to help diagnose, treat, or inform the user as to their physiological status. By acting on this information, the overall health of the user may be improved.

Illustrative System

FIG. 1 is an illustrative system 100 that may include a user 102 and a wearable device 104 that uses radio frequency (RF) signals 108 to determine molecular concentrations of molecules of interest in at least a portion of the user's 102 body, according to one implementation.

The user 102 may have one or more devices on or about their person, such as the wearable device 104. The wearable device 104 may be implemented in various physical form factors including, but not limited to, the following: wrist bands, torcs, arm bands, and so forth.

The user's 102 body contains one or more different types of molecules 106. For example, the blood of the user 102 may include glucose, water, creatinine, and so forth. Sometimes the body may include molecules 106 that are exogenous. For example, if the user 102 consumes alcohol, inhales carbon monoxide, absorbs a pesticide through the skin, and so forth, presence or concentration of those types of molecules 106 may be determined in the dermis, within the blood, or other tissues within the body. As described below, a radio frequency (RF) signal 108 may be used to determine information about one or more molecules 106.

The wearable device 104 may include at least one support structure 110 that supports one or more of the following components. For example, the wearable device 104 may comprise a housing or capsule that is attached to a wrist band, allowing the wearable device 104 to be retained on the wrist of the user 102.

The wearable device 104 includes one or more antennas 112. The one or more antennas 112 may be mounted to the support structure 110. The antennas 112 may comprise two or more antenna elements in particular arrangements. For example, the antenna 112 may comprise a first antenna element and one or more other antenna elements with variable distances between one another. The arrangement of antenna elements is discussed in more detail below with regard to FIGS. 4-7. In some implementations the wearable device 104 may include antennas 112 with different configurations or geometries, allowing for operation at different sample depths.

The antenna elements within a particular antenna 112 are connected to one or more radio frequency (RF) transceivers 114. In one implementation each antenna 112 may be connected to a particular RF transceiver 114. In other implementations, a single RF transceiver 114 may be connected via a switching network to two or more antennas 112.

The RF transceiver 114 may comprise an oscillator 116, a transmitter 118, and a receiver 120. The oscillator 116 may be used to provide a reference frequency for operation of the transmitter 118, the receiver 120, a clock (not shown), and so forth. The transmitter 118 is configured to generate the RF signal 108. The transmitter 118 may be able to generate RF signals 108 at one or more frequencies, in one or more frequency bands or ranges, and so forth. For example, the transmitter 118 may be able to generate RF signals 108 at one or more of the 5 GHz, 10 GHz, 50 GHz, 75 GHz, 100 GHz, or other bands. The RF signal 108 that is generated may be modulated with a continuous wave.

During transmission, the transmitter 118 provides the RF signal 108 to one or more of the antenna elements in one or more antennas 112. For example, output from the transmitter 118 may be connected to a first antenna element in the antenna 112. The antennas 112 emit the signal 108 which then impinges on the body of the user 102 while the device 104 is being worn or held close to the user 102.

In some implementations, during reception, one or more of the antenna elements in the antenna 112 that are not connected to the transmitter 118 are connected to an input of the receiver 120. Continuing the example above, the receiver 120 may be connected to the second antenna element in the antenna 112. The receiver 120 detects the RF signal 108. The receiver 120 may comprise analog hardware, digital hardware, or a combination thereof. For example, the receiver 120 may comprise a direct sampling software defined radio (SDR). In another example, the RF signal 108 as acquired by the one or more antennas 112 may be mixed with output from the oscillator 116. In other implementations the same antenna element of the antenna 112 may be connected to the transmitter 118 and the receiver 120 simultaneously using one or more directional couplers, duplexers, or other devices.

The RF transceiver 114 may be configurable to operate in simplex, duplex, or combinations thereof. For example, the RF transceiver 114 may be configurable to transmit on one band while receiving on another band. In one implementation, the RF transceiver 114 may comprise the BGT24LTR11 device from Infineon Technologies AG that is capable of transmitting and receiving in the 24 GHz band.

While a RF transceiver 114 is shown, it is understood that in other implementations other components such as a discrete transmitter 118 and receiver 120 could be used.

A control module 122 may be used to direct operation of the RF transceivers 114 or other components. For example, the control module 122 may comprise a hardware processor (processor) executing instructions that operate one or more of the transmitters 118 to transmit particular signals at particular frequencies at particular times, to operate one or more of the receivers 120 to receive the signals 108 generated by the one or more transmitters 118, to operate a switching device or other circuitry to connect one or more particular antennas 112 to the transmitter 118 output, to operate a switching device or other circuitry to connect one or more particular antennas 112 to the input of the receiver 120, and so forth.

The control module 122 may use one or more data acquisition parameters 124 to control operation. For example, the data acquisition parameters 124 may specify a sample frequency that indicates how often to transmit and receive signals 108, sample depth within the user 102 to be used, and so forth. In some implementations the data acquisition parameters 124 may be specific to a particular type of molecule 106 that is being detected. For example, the data acquisition parameters 124 for glucose may have a first sample depth that is different from a second sample depth used for organophosphates. The data acquisition parameters 124 may reference specific operating parameters 126.

The operating parameters 126 may specify one or more of frequency, output power, modulation, signal duration, particular antenna 112 used to emit the signal 108, particular antenna 112 to acquire the signal 108, and so forth. For example, the operating parameters 126 may specify that a signal 108 is to be transmitted with a center frequency of 5.201 GHz at 0 dBm, continuous wave (CW) modulation, for 1 ms using a chirp with ascending frequency from 5.200 to 5.202 GHz, emitted from the antenna 112.

The operating parameters 126 may relate a sample depth specified by the data acquisition parameters 124 to a particular antenna configuration. For example, the data acquisition parameters 124 may indicate a depth in terms of linear measurement such as millimeters or with a relative indicator such as "shallow", "medium", or "deep". Responsive to the data acquisition parameters 124, the control module 122 may determine operating parameters 126 that are indicative of a particular antenna configuration. For example, a "shallow" sample depth may correspond to a first antenna 112(1) with a first antenna configuration. In comparison, a "deep" sample depth may correspond to a second antenna 112(2) with a second antenna configuration.

Once the operating parameters 126 have been determined, the control module 122 or another component may operate the circuitry in the wearable device 104. For example, first circuitry may be operated to selectively couple the output from the transmitter 118 to the first antenna element and second circuitry may be operated to selectively couple the input to the receiver 120 to the second antenna element.

The receivers 120 produce signal characteristic values 128 that are representative of the received signals. The signal characteristic values 128 may include, but are not limited to, frequency data 130, phase data 132, amplitude data 134, and so forth. Frequency data 130 is indicative of frequency of the received signal. The phase data 132 provides information about the phase of the received signal, and in some implementations may be used to determine a phase difference between the transmitted signal and the received signal. The amplitude data 134 provides information indicative of amplitude of the received signal. For example, the amplitude data 134 may indicate a received signal strength at different frequencies. Other signal characteristic values 128 may include received signal polarization.

As the RF signals 108 pass through the body of the user 102, they are affected by the molecules 106 therein. Various interactions take place between the signals 108 and the molecules 106. For example, the presence of glucose in the body along the line extending from the antenna 112(1) that is emitting the signal 108 and the antenna 112(2) that is acquiring the signal 108 may result in a change in the phase of the received signal, relative to the transmitted signal. In some implementations, a phase difference that is indicative of this change in phase of the received signal relative to the transmitted signal, may be indicative of the concentration of glucose. For example, with no glucose present a 0 degree phase difference may be detected, while a 0.004 degree phase difference may be associated with the presence of glucose. As described below, a presence or concentration of a type of molecule 106 may be determined based on the phase difference or other signal characteristics.

A data processing module 136 may use one or more of the operating parameters 126 of the transmitted signal(s) or the signal characteristic values 128 of the received signal(s) as input. The data processing module 136 may also access molecular reference data 138. The molecular reference data 138 comprises information that, for a particular type of molecule 106, associates one or more signal characteristics with information such as concentration of the particular type of molecule 106. The molecular reference data 138 may be general or specific to a particular user 102. For example, the molecular reference data 138 may be generated and associated with particular user 102(1) "Pat".

The data processing module 136 uses the signal characteristic value(s) 128 and the molecular reference data 138 to determine molecular concentration data 140. The molecular concentration data 140 may specify a mass per unit volume. For example, the signal characteristic value 128 indicates the phase difference at a particular frequency is 0.004 degrees. This value may be used as input to the molecular reference data 138 which corresponds to molecular concentration data 140 indicative of a mass per volume, such as a glucose concentration of 159 milligrams per deciliter (md/dL).

As described below in more detail, the signal characteristic values 128 may be obtained for a plurality of different frequencies and may be obtained using a variety of different combinations of antennas 112 to emit and acquire the signals 108. The signal characteristic values 128 may be used to determine the molecular concentration data 140 for one or more different types of molecules 106. For example, the molecular concentration data 140 may indicate the concentration of glucose and water in the body of the user 102.

The wearable device 104 may include, or receive data from, one or more other sensors 142. For example, a temperature sensor may be used to provide an indication of the body temperature of the user 102. The body temperature may then be used as an input to the data processing module 136 to improve the accuracy of the molecular concentration data 140. These sensors 142 are discussed in more detail below with regard to FIG. 2. In other implementations data from the sensors 142 may be obtained to provide other information about physiological status, activity level, and so forth.

Output from the sensors 142 may also be used to determine operation of the data processing module 136. For example, the sensors 142 may include one or more accelerometers. If the accelerometers detect motion that exceeds a threshold value, the data processing module 136 may be operated to determine molecular concentration data 140. For example, if the user 102 has been running, the system may operate to determine glucose concentration. In another example, if the motion of the user 102 is less than a threshold value, the data processing module 136 may be operated to determine molecular concentration data 140. For example, if no movement has been detected for 2 minutes, such as if the user is asleep or unconscious, the data processing module 136 may be operated to determine molecular concentration data 140.

A user interface module 144 may be configured to use the molecular concentration data 140 and produce output data 146. For example, based on the molecular concentration data 140 indicating that the blood glucose level is below a threshold value, output data 146 may be generated. One or more output devices 148 may be used to present a user interface based on at least a portion of the output data 146. Continuing the example, the user interface module 144 may produce output data 146 that comprises instructions to operate a speaker to present an audible prompt indicating a low blood glucose level. In another example, the output data 146 may be provided to an other device 150. For example, the wearable device 104 may be connected via Bluetooth or another wireless protocol to a smartphone, wireless access point, in vehicle computer system, or other device. Based on the output data 146 the other device 150 may present an output to the user 102, alert someone else, modify operation of another device, and so forth. For example, if the wearable device 104 provides data to a vehicle that indicates the user 102 in the driver's seat has a concentration of alcohol that exceeds a threshold value, the vehicle may be prevented from moving, or may only be able to operate in a fully autonomous mode.

Figure 2:
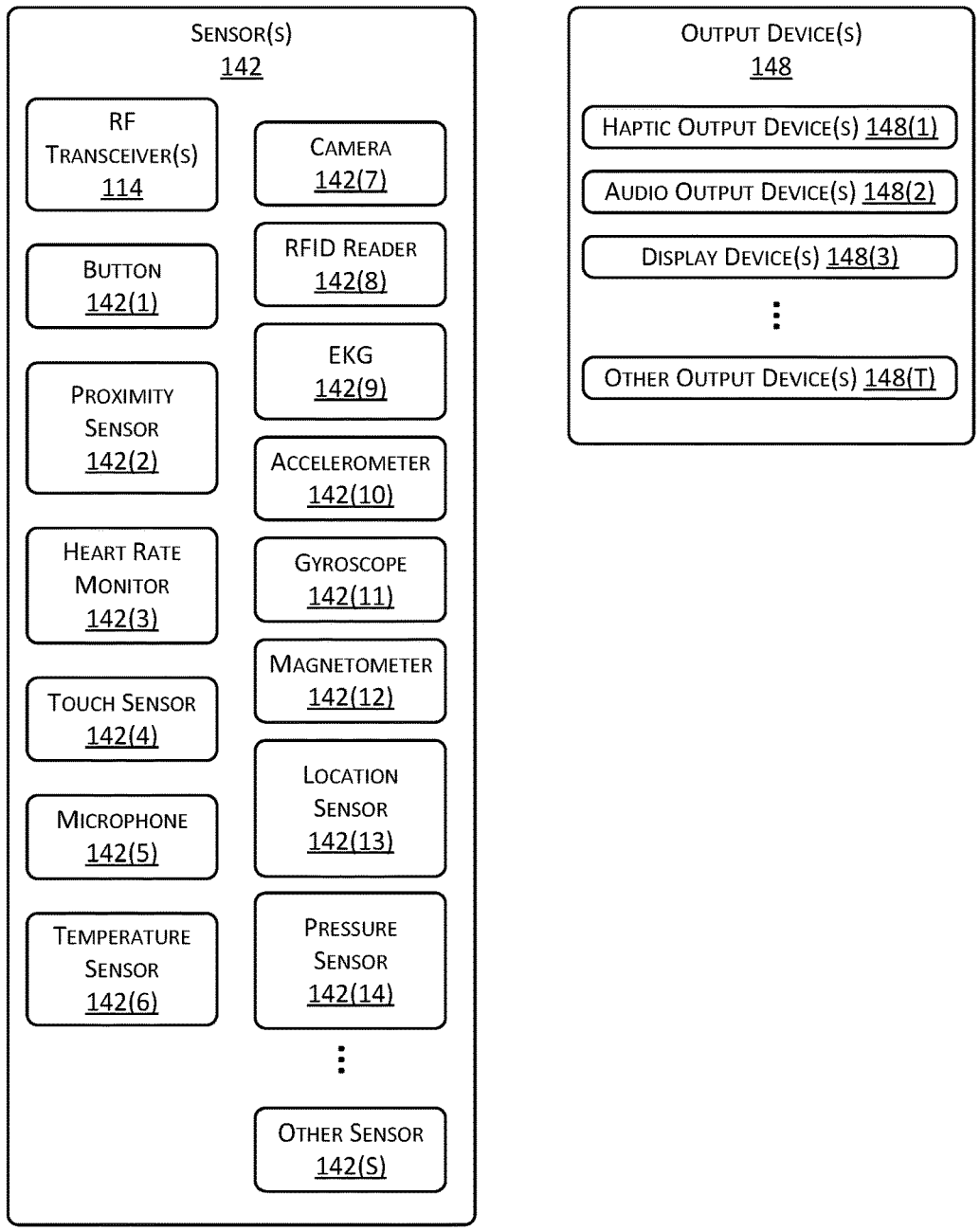
FIG. 2 illustrates a block diagram of sensors and output devices that may be used by computing device(s) during operation, according to one implementation.

FIG. 2 illustrates a block diagram 200 of sensors 142 and output devices 148 that may be used by the devices of the system 100 during operation.

One or more sensors 142 may be integrated with or internal to the wearable device 104 or the other device 150. For example, the sensors 142 may be built-in to the wearable device 104 during manufacture. In other implementations, the sensors 142 may be part of another device which is in communication with the wearable device 104. For example, the sensors 142 may comprise a device external to, but in communication with, the wearable device 104 using Bluetooth, Wi-Fi, 3G, 4G, 5G, LTE, ZigBee, Z-Wave, or another wireless or wired communication technology.

The sensors 142 may include the RF transceivers 114.

The one or more sensors 142 may include one or more buttons 142(1) that are configured to accept input from the user 102. The buttons 142(1) may comprise mechanical, capacitive, optical, or other mechanisms. For example, the buttons 142(1) may comprise mechanical switches configured to accept an applied force from a touch of the user 102 to generate an input signal.

A proximity sensor 142(2) may be configured to provide sensor data 324 indicative of one or more of a presence or absence of an object, a distance to the object, or characteristics of the object. The proximity sensor 142(2) may use optical, electrical, ultrasonic, electromagnetic, or other techniques to determine a presence of an object. For example, the proximity sensor 142(2) may comprise a capacitive proximity sensor configured to provide an electrical field and determine a change in electrical capacitance due to presence or absence of an object within the electrical field.

A heart rate monitor 142(3) or pulse oximeter may be configured to provide sensor data 324 that is indicative of a cardiac pulse rate, and data indicative of oxygen saturation of the user's 102 blood, and so forth. For example, the heart rate monitor 142(3) may use an optical emitter such as one or more light emitting diodes (LEDs) and a corresponding optical detector such as a photodetector to perform photoplethysmography, determine cardiac pulse, determine changes in apparent color of the blood of the user 102 resulting from oxygen binding with hemoglobin in the blood, and so forth.

The sensors 142 may include one or more touch sensors 142(4). The touch sensors 142(4) may use resistive, capacitive, surface capacitance, projected capacitance, mutual capacitance, optical, Interpolating Force-Sensitive Resistance (IFSR), or other mechanisms to determine the position of a touch or near-touch of the user 102. For example, the IFSR may comprise a material configured to change electrical resistance responsive to an applied force. The location within the material of that change in electrical resistance may indicate the position of the touch.

One or more microphones 142(5) may be configured to acquire information about sound present in the environment. In some implementations, arrays of microphones 142(5) may be used. These arrays may implement beamforming techniques to provide for directionality of gain. The one or more microphones 142(5) may be used to acquire audio data, such as speech from the user 102.

A temperature sensor (or thermometer) 142(6) may provide information indicative of a temperature of an object. The temperature sensor 142(6) in may be configured to measure ambient air temperature proximate to the user 102, the body temperature of the user 102, and so forth. The temperature sensor 142(6) may comprise a silicon bandgap temperature sensor, thermistor, thermocouple, or other device. In some implementations, the temperature sensor 142(6) may comprise an infrared detector configured to determine temperature using thermal radiation.

The sensors 142 may include one or more cameras 142(7). The cameras 142(7) may comprise a charge couple device, complementary oxide semiconductor, or other image sensor that is able to acquire images.

One or more radio frequency identification (RFID) readers 142(8), near field communication (NFC) systems, and so forth, may also be included as sensors 142. The user 102, objects around the computing device, locations within a building, and so forth, may be equipped with one or more radio frequency (RF) tags. The RF tags are configured to emit an RF signal. In one implementation, the RF tag may be a RFID tag configured to emit the RF signal upon activation by an external signal. For example, the external signal may comprise a RF signal or a magnetic field configured to energize or activate the RFID tag. In another implementation, the RF tag may comprise a transmitter and a power source configured to power the transmitter. For example, the RF tag may comprise a Bluetooth Low Energy (BLE) transmitter and battery. In other implementations, the tag may use other techniques to indicate its presence. For example, an acoustic tag may be configured to generate an ultrasonic signal, which is detected by corresponding acoustic receivers. In yet another implementation, the tag may be configured to emit an optical signal.

The sensors 142 may include an electrocardiograph 142(9) that is configured to detect electrical signals produced by the heart of the user 102.

The sensors 142 may include one or more accelerometers 142(10). The accelerometers 142(10) may provide information such as the direction and magnitude of an imposed acceleration. Data such as rate of acceleration, determination of changes in direction, speed, and so forth, may be determined using the accelerometers 142(10).

A gyroscope 142(11) provides information indicative of rotation of an object affixed thereto. For example, the gyroscope 142(11) may indicate whether the device has been rotated.

A magnetometer 142(12) may be used to determine an orientation by measuring ambient magnetic fields, such as the terrestrial magnetic field. For example, output from the magnetometer 142(12) may be used to determine whether the device containing the sensor 142, such as a computing device, has changed orientation or otherwise moved. In other implementations, the magnetometer 142(12) may be configured to detect magnetic fields generated by another device.

A location sensor 142(13) is configured to provide information indicative of a location. The location may be relative or absolute. For example, a relative location may indicate "kitchen", "bedroom", "conference room", and so forth. In comparison, an absolute location is expressed relative to a reference point or datum, such as a street address, geolocation comprising coordinates indicative of latitude and longitude, grid square, and so forth. The location sensor 142(13) may include, but is not limited to, radio navigation-based systems such as terrestrial or satellite-based navigational systems. The satellite-based navigation system may include one or more of a Global Positioning System (GPS) receiver, a Global Navigation Satellite System (GLONASS) receiver, a Galileo receiver, a BeiDou Navigation Satellite System (BDS) receiver, an Indian Regional Navigational Satellite System, and so forth. In some implementations, the location sensor 142(13) may be omitted or operate in conjunction with an external resource such as a cellular network operator providing location information, or Bluetooth beacons.

A pressure sensor 142(14) may provide information about the pressure between a portion of the wearable device 104 and a portion of the user 102. For example, the pressure sensor 142(14) may comprise a capacitive element, strain gauge, spring-biased contact switch, or other device that is used to determine the amount of pressure between the user's 102 arm and an inner surface of the wearable device 104 that is in contact with the arm. In some implementations the pressure sensor 142(14) may provide information indicative of a force measurement, such as 0.5 Newtons, a relative force measurement, or whether the pressure is greater than a threshold value.

In some implementations, operation of one or more components in the wearable device 104 may be based at least in part on information from the pressure sensor 142(14). For example, based on data provided by the pressure sensor 142(14) a determination may be made as to whether at least a portion of the wearable device 104 is in contact with the user 102 or another object. Continuing the example, if the pressure indicated by the pressure sensor 142(14) exceeds a threshold value, the wearable device 104 may be determined to be in contact with the user 102. Based on this determination that the wearable device 104 is in contact with the user 102, one or more of the transmitter 118, receiver 120, sensors 142, and so forth may be operated. Likewise, data from the pressure sensor 142(14) may be used to determine the wearable device 104 is not in sufficient physical contact with the user 102. As a result, one or more of the transmitter 118, receiver 120, sensors 142, and so forth may be turned off.

The sensors 142 may include other sensors 142(S) as well. For example, the other sensors 142(S) may include strain gauges, anti-tamper indicators, and so forth. For example, strain gauges or strain sensors may be embedded within the wearable device 104 and may be configured to provide information indicating that at least a portion of the wearable device 104 has been stretched or displaced such that the wearable device 104 may have been donned or doffed.

In some implementations, the sensors 142 may include hardware processors, memory, and other elements configured to perform various functions. Furthermore, the sensors 142 may be configured to communicate by way of the network or may couple directly with the computing device.

The computing device may include or may couple to one or more output devices 148. The output devices 148 are configured to generate signals which may be perceived by the user 102, detectable by the sensors 142, or a combination thereof.

Haptic output devices 148(1) are configured to provide a signal, which results in a tactile sensation to the user 102. The haptic output devices 148(1) may use one or more mechanisms such as electrical stimulation or mechanical displacement to provide the signal. For example, the haptic output devices 148(1) may be configured to generate a modulated electrical signal, which produces an apparent tactile sensation in one or more fingers of the user 102. In another example, the haptic output devices 148(1) may comprise piezoelectric or rotary motor devices configured to provide a vibration that may be felt by the user 102.

One or more audio output devices 148(2) are configured to provide acoustic output. The acoustic output includes one or more of infrasonic sound, audible sound, or ultrasonic sound. The audio output devices 148(2) may use one or more mechanisms to generate the acoustic output. These mechanisms may include, but are not limited to, the following: voice coils, piezoelectric elements, magnetostrictive elements, electrostatic elements, and so forth. For example, a piezoelectric buzzer or a speaker may be used to provide acoustic output by an audio output device 148(2).

The display devices 148(3) may be configured to provide output that may be seen by the user 102 or detected by a light-sensitive detector such as an image sensor or light sensor. The output may be monochrome or color. The display devices 148(3) may be emissive, reflective, or both. An emissive display device 148(3), such as using light emitting diodes (LEDs), is configured to emit light during operation. In comparison, a reflective display device 148(3), such as using an electrophoretic element, relies on ambient light to present an image. Backlights or front lights may be used to illuminate non-emissive display devices 148(3) to provide visibility of the output in conditions where the ambient light levels are low.

The display mechanisms of display devices 148(3) may include, but are not limited to, micro-electromechanical systems (MEMS), spatial light modulators, electroluminescent displays, quantum dot displays, liquid crystal on silicon (LCOS) displays, cholesteric displays, interferometric displays, liquid crystal displays, electrophoretic displays, LED displays, and so forth. These display mechanisms are configured to emit light, modulate incident light emitted from another source, or both. The display devices 148(3) may operate as panels, projectors, and so forth.

The display devices 148(3) may be configured to present images. For example, the display devices 148(3) may comprise a pixel-addressable display. The image may comprise at least a two-dimensional array of pixels or a vector representation of a two-dimensional image.

In some implementations, the display devices 148(3) may be configured to provide non-image data, such as text or numeric characters, colors, and so forth. For example, a segmented electrophoretic display device, segmented LED, and so forth, may be used to present information such as letters or numbers. The display devices 148(3) may also be configurable to vary the color of the segment, such as using multicolor LED segments.

Other output devices 148(T) may also be present.

Figure 3:
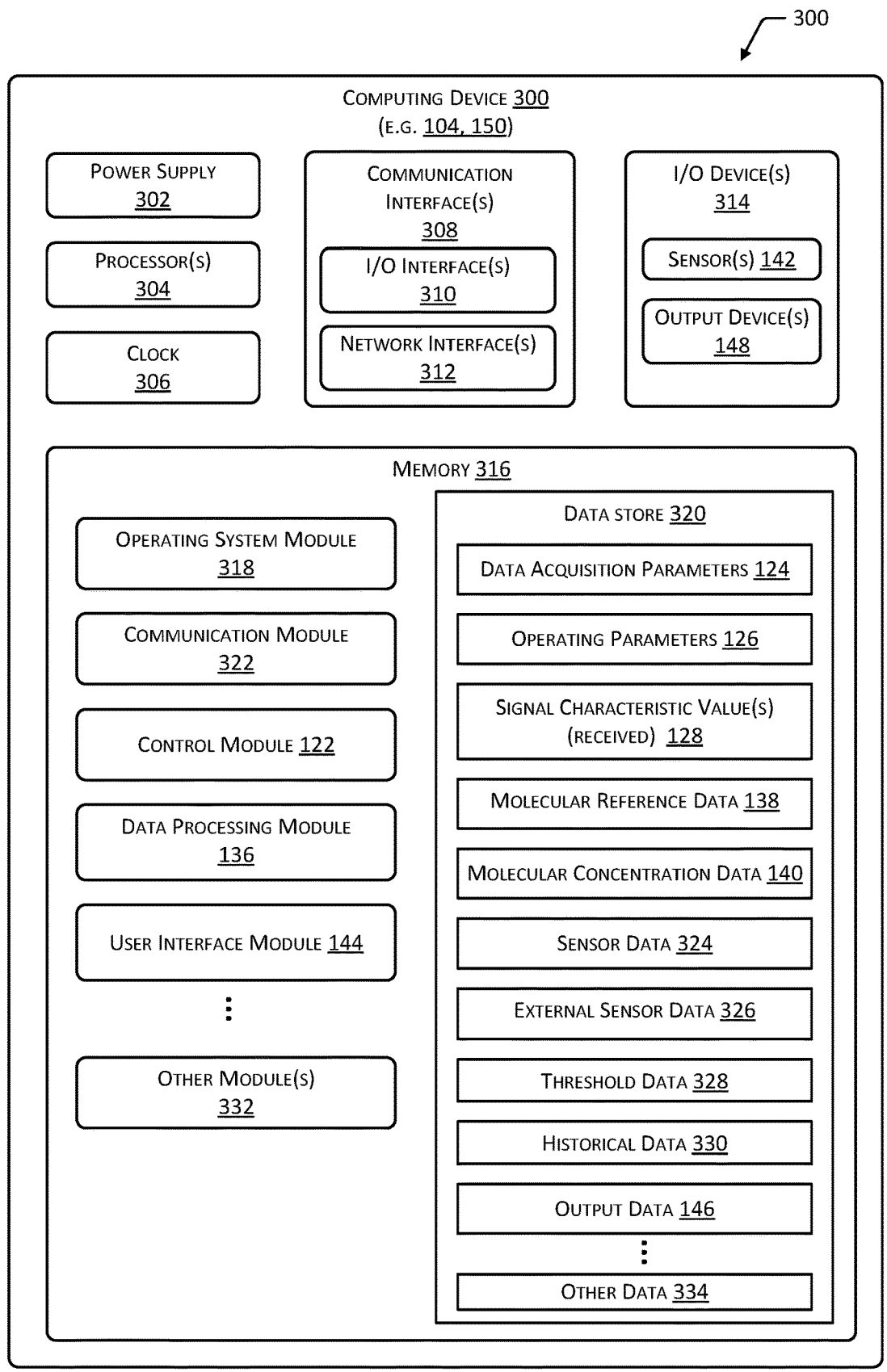
FIG. 3 illustrates a block diagram of a computing device(s) that may be included in or in communication with the measurement device, according to one implementation.

FIG. 3 illustrates a block diagram of a computing device 300 configured to support operation of the system 100. As described above, the computing device 300 may be the wearable device 104, the other device 150, and so forth.

One or more power supplies 302 are configured to provide electrical power suitable for operating the components in the computing device 300. In some implementations, the power supply 302 may comprise a rechargeable battery, fuel cell, photovoltaic cell, power conditioning circuitry, and so forth.

The computing device 300 may include one or more hardware processors 304 (processors) configured to execute one or more stored instructions. The processors 304 may comprise one or more cores. One or more clocks 306 may provide information indicative of date, time, ticks, and so forth. For example, the processor 304 may use data from the clock 306 to generate a timestamp, trigger a preprogrammed action, and so forth.

The computing device 300 may include one or more communication interfaces 308 such as input/output (I/O) interfaces 310, network interfaces 312, and so forth. The communication interfaces 308 enable the computing device 300, or components thereof, to communicate with other devices or components. The communication interfaces 308 may include one or more I/O interfaces 310. The I/O interfaces 310 may comprise interfaces such as Inter-Integrated Circuit (I2C), Serial Peripheral Interface bus (SPI), Universal Serial Bus (USB) as promulgated by the USB Implementers Forum, RS-232, and so forth.

The I/O interface(s) 310 may couple to one or more I/O devices 314. The I/O devices 314 may include input devices such as one or more of a camera 142(7), a sensor 142, keyboard, mouse, scanner, and so forth. The I/O devices 314 may also include output devices 148 such as one or more of a display device 148(3), printer, audio output device 148(2), and so forth. In some embodiments, the I/O devices 314 may be physically incorporated with the computing device 300 or may be externally placed.

The network interfaces 312 are configured to provide communications between the computing device 300 and other devices, such as the sensors 142, routers, access points, and so forth. The network interfaces 312 may include devices configured to couple to wired or wireless personal area networks (PANs), local area networks (LANs), wide area networks (WANs), and so forth. For example, the network interfaces 312 may include devices compatible with Ethernet, Wi-Fi, Bluetooth, ZigBee, 4G, 5G, LTE, and so forth.

The computing device 300 may also include one or more busses or other internal communications hardware or software that allow for the transfer of data between the various modules and components of the computing device 300.

As shown in FIG. 3, the computing device 300 includes one or more memories 316. The memory 316 comprises one or more computer-readable storage media (CRSM). The CRSM may be any one or more of an electronic storage medium, a magnetic storage medium, an optical storage medium, a quantum storage medium, a mechanical computer storage medium, and so forth. The memory 316 provides storage of computer-readable instructions, data structures, program modules, and other data for the operation of the computing device 300. A few example functional modules are shown stored in the memory 316, although the same functionality may alternatively be implemented in hardware, firmware, or as a system on a chip (SOC).

The memory 316 may include at least one operating system (OS) module 318. The OS module 318 is configured to manage hardware resource devices such as the I/O interfaces 310, the network interfaces 312, the I/O devices 314, and provide various services to applications or modules executing on the processors 304. The OS module 318 may implement a variant of the FreeBSD operating system as promulgated by the FreeBSD Project; other UNIX or UNIX-like operating system; a variation of the Linux operating system as promulgated by Linus Torvalds; the Windows operating system from Microsoft Corporation of Redmond, Washington, USA; the Android operating system from Google Corporation of Mountain View, California, USA; the iOS operating system from Apple Corporation of Cupertino, California, USA; or other operating systems.

Also stored in the memory 316 may be a data store 320 and one or more of the following modules. These modules may be executed as foreground applications, background tasks, daemons, and so forth. The data store 320 may use a flat file, database, linked list, tree, executable code, script, or other data structure to store information. In some implementations, the data store 320 or a portion of the data store 320 may be distributed across one or more other devices including the computing devices 300, network attached storage devices, and so forth.

A communication module 322 may be configured to establish communications with one or more of other computing devices 300, the sensors 142, or other devices 150. The communications may be authenticated, encrypted, and so forth. The communication module 322 may also control the communication interfaces 308.

One or more of the data acquisition parameters 124, operating parameters 126, signal characteristic values 128, molecular reference data 138, or the molecular concentration data 140 may be stored in the memory 316.

The memory 316 may also store the control module 122. As described above, the control module 122 may operate the RF transceivers 114 to produce signal characteristic values 128.

The memory 316 may store the data processing module 136. The data processing module 136 uses the signal characteristic values 128, the molecular reference data 138, and so forth as input to generate the molecular concentration data 140.

In one implementation, the data processing module 136 may use molecular reference data 138 to generate molecular concentration data 140 that is indicative of a concentration of one or more types of molecules 106 in the user 102.

In some implementations, a calibration process may be performed in which an external sensor is used to obtain external sensor data 326 that is indicative of a concentration of a type of molecule 106. For example, a blood glucose meter that uses a sample of a drop of blood may be used as the external sensor. At a contemporaneous time, the RF transceivers 114 may be used to obtain the signal characteristic values 128. The external sensor data 326 comprising concentration data from the external sensor may be used in conjunction with the signal characteristic values 128 to determine a correspondence between one or more signal characteristic values 128 and molecular concentration. This correspondence may be stored as the molecular reference data 138. The molecular reference data 138 may be specific to a particular user 102. For example, the molecular reference data 138 may be specific to user 102 "Pat". In some implementations, the molecular reference data 138 may be processed using one or more techniques to interpolate values between those which have been measured. In some implementations, previously acquired molecular reference data 138 may be used, and a calibration factor may be determined based on the molecular reference data 138.

Threshold data 328 may be stored in the memory 316. The threshold data 328 may be used to designate a threshold to which molecular concentration data 140 may be compared. For example, the threshold data 328 may specify threshold values for particular types of molecules 106. If the molecular concentration data 140 is less than a first threshold or greater than a second threshold, the user interface module 144 may generate an alarm and present that information using the output device 148.

The user interface module 144 provides a user interface using one or more of the I/O devices 314. The user interface module 144 may be used to obtain input from the user 102, present information to the user 102, and so forth. For example, the user interface module 144 may present a graphical user interface on the display device 148(3) and accept user input using the touch sensor 142(4).

Continuing the earlier example, if the molecular concentration data 140 indicates that user's 102 blood glucose level is less than a threshold value, the user interface module 144 may present information indicative of this on the display device 148(3). The user 102 may then take corrective actions, such as consuming glucose to raise their blood sugar level, reducing activity, and so forth.

The computing device 300 may maintain historical data 330. For example, the historical data 330 may comprise the signal characteristic values 128, molecular concentration data 140, or sensor data 324 from one or more of the sensors 142 obtained at different times. The historical data 330 may be used to provide information about trends or changes over time. For example, the historical data 330 may comprise an indication of average daily blood glucose levels of the user 102 over a span of several weeks. The user 102 may then use this data to assist in managing their diet and insulin dosage.

Other modules 332 may also be present in the memory 316, as well as other data 334 in the data store 320.

In different implementations, different computing devices 300 may have different capabilities or capacities. For example, the other device 150 may have significantly more processor 304 capability and memory 316 capacity compared to the wearable device 104. In one implementation, the wearable device 104 may determine the signal characteristic values 128 and send those values to the other device 150. Other combinations of distribution of data processing and functionality may be used in other implementations.

Figure 4:
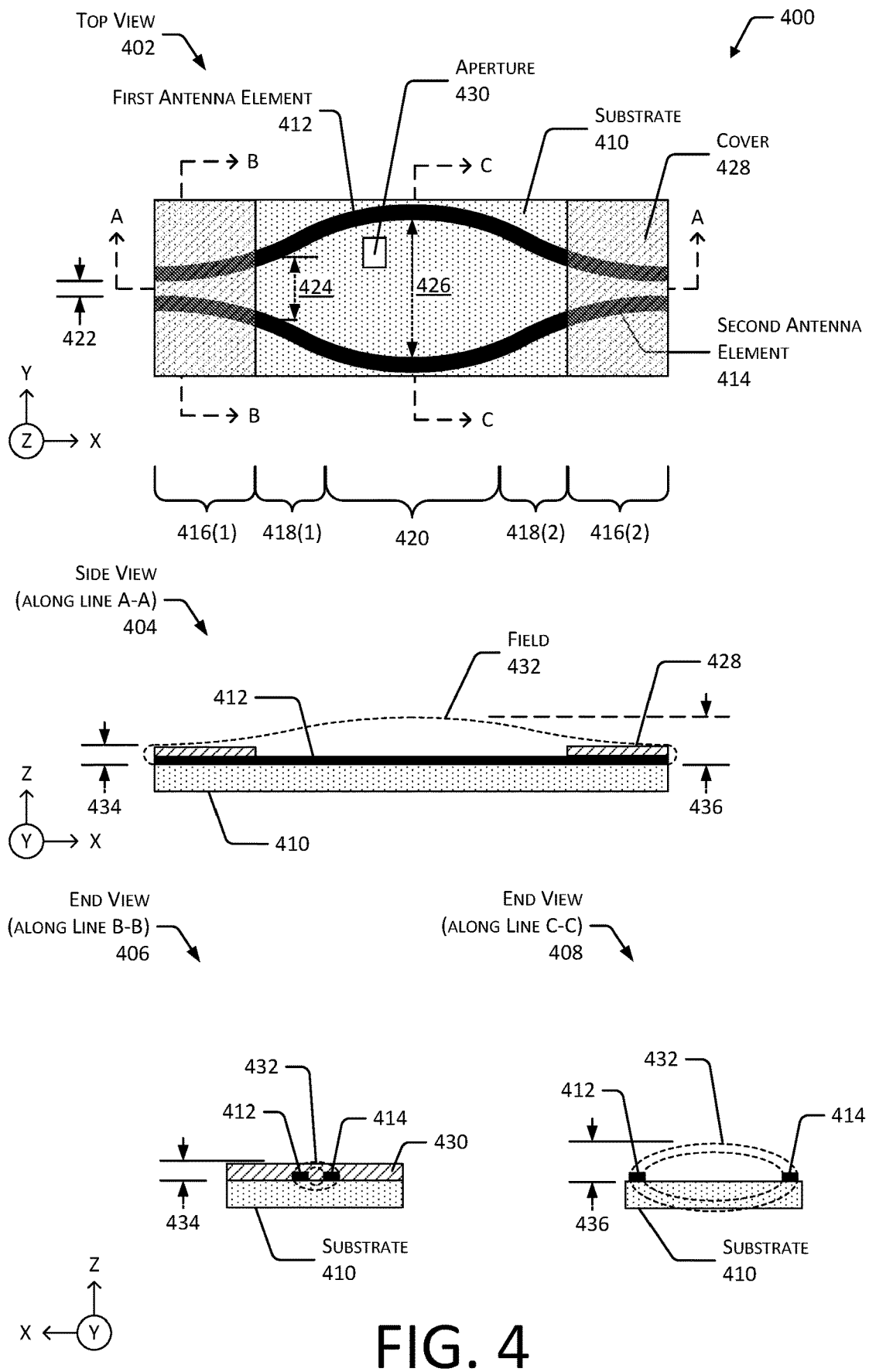
FIG. 4 illustrates a first implementation of the antenna in a slotline configuration.

FIG. 4 illustrates a first implementation 400 of the antenna 112 in a slotline configuration. Depicted are a top view 402, a side view 404 of a cross section along a centerline of the antenna 112, an end view 406 of a first cross section perpendicular to the centerline, and an end view 408 of a second cross section perpendicular to the centerline.

The antenna 112 comprises a substrate 410. The substrate 410 may comprise an electrical insulator such as plastic, glass, fiberglass, and so forth. For example, the substrate 410 may comprise a dielectric. A first antenna element 412 and a second antenna element 414 may be affixed to a first surface of the substrate 410. The antenna elements may comprise a wire, trace, or other electrically conductive material.

A geometry or relative arrangement of the antenna elements may be described in terms of three sections. While the geometry depicted here is symmetrical with respect to two axes, asymmetrical designs are also possible, such as described below with regard to FIG. 7.

For ease of discussion, and not necessarily as a limitation, the antenna 112 is shown divided into a pair of first sections 416(1) and 416(2), a pair of second sections 418(1) and 418(2), and a third section 420. The first section 416(1) is proximate to a first end of the antenna 112 while the first section 416(2) is proximate to a second end of the antenna 112. The second section 418(1) is adjacent to the first section 416(1) and the second section 418(2) is adjacent to the first section 416(2). The third section 420 is between the second section 418(1) and the second section 418(2).

Proximate to the first end of the antenna 112, the first antenna element 412 and the second antenna element 414 are separated from one another by a distance 422. For example, a first point on the first antenna element 412 and a second point on the second antenna element 414 that are both a first distance from the first end of the antenna 112 may be separated by the distance 422.

The first section 416 may include the terminals, contacts, or other structure to which other circuitry is attached to the antenna elements. The first section 416 may exhibit a first impedance at a specified frequency. For example, the first section 416 may exhibit an impedance that matches an impedance of the RF transceiver 114 at a frequency used by the RF transceiver 114.

As the distance from the first end increases, the spacing between the first antenna element 412 and the second antenna element 414 increases. For example, within the second section 418(1) that is a second distance from the first end of the antenna 112, the first antenna element 412 and the second antenna element 414 are a second distance 424 apart. The second distance 424 is greater than the first distance 422.

The antenna elements are separated with a geometry that avoids discontinuities such as two straight line sections meeting at a vertex. Instead, the antenna elements gradually separate and merge due to the curvature of the antenna elements. By avoiding discontinuities, the antenna 112 avoids an abrupt change in impedance which would introduce reflections of the signals on the antenna 112.

Within the third section 420 that is shown here centered on a midpoint between the first end and the second end, the first antenna element 412 and the second antenna element 414 are a third distance 426 apart. The third distance 426 is greater than the second distance 424. The impedance in the third section 420 differs from the impedance in the first section 416. Due to the third distance 426 being greater than the first distance 422, the fringe effect of the electric field associated with the signal 108 in the antenna 112 is increased, as shown below, resulting in an increased sample depth for the signal 108.

In some implementations a cover 428 may be used that is adjacent to the antenna elements and is between the antenna elements and the user 102. The cover 428 may comprise a non-conductive material. For example, the cover 428 may comprise plastic, glass, and so forth. The cover 428 may be transparent to the signal(s) 108.

In the implementation depicted, the cover 428 is arranged atop the first sections 416(1) and 416(2) while the portion of the first antenna element 412 and the second antenna element 414 in the second sections 418(1) and 418(2) and the third section 420 may come into direct contact with the skin of the user 102. In other implementations the cover 428 may cover all sections of the antenna 112 or may be omitted.

The antenna elements may comprise a biocompatible material such as gold, silver, rhodium, and so forth. In addition to being used to emit and acquire the signal 108, in implementations where the antenna elements are in contact with the user 102, they may be used to acquire other information. For example, galvanic skin conductivity may be measured using two or more antenna elements, cardiac electrical signals may be acquired using one or more of the antenna elements, and so forth.

The antenna elements may be on, affixed to, incorporated within, or otherwise maintained by the substrate 410. The substrate 410 may be rigid or flexible. For example, the substrate 410 may comprise a plastic layer upon which the antenna elements have been deposited, printed, adhered, and so forth. In one implementation the antenna 112 may comprise a flexible printed circuit with the antenna elements comprising traces thereon.

One or more apertures 430 or sensors 142 (not shown) may be located between or near the antenna elements of the antenna 112. The aperture 430 may provide a window or opening in the substrate 410 to facilitate operation of the wearable device 104. For example, the aperture 430 may provide a window through which an optical sensor such as a light emitting diode (LED) or a camera 142(7) is able to operate and acquire data about the user 102. In another example, the aperture 430 may be used by another sensor 142, such as a capacitive sensor, pressure sensor 142(14), and so forth. Some devices may be mounted to the substrate 410 or may be located between the antenna 112 and the user 102 during operation. For example, an LED may be affixed to the substrate 410 and when operated may illuminate a portion of the user 102 that is proximate to the inner surface of the wearable device 104. In some implementations sensors 142 may operate through the substrate 410. For example, if the substrate 410 is flexible a pressure sensor 142(14) may operate through the substrate 410. In another example the substrate 410 may be transmissive to a signal being detected, such as a particular frequency of light.

The side view 404 depicts a cross section of the antenna 112 along a centerline indicated by line A-A. Shown in this view is a representation of an electric field 432 associated with a signal 108. In the first sections 416(1) and 416(2) the field 432 extends a distance 434 from the substrate 410. In the third section 420 the field 432 extends a distance 436 from the substrate 410, where distance 436 is greater than distance 434. During use, the antenna 112 is placed proximate to the user 102 such that the field 432 impinges on at least a portion of the user 102. For example, the antenna 112 may be arranged such that the portion of the first antenna element 412 and the second antenna element 414 in the third section 420 are in contact with the skin of the user 102. During operation, the field 432 extends into the user 102.

The end view 406 along line B-B also shows the distance 434 while the end view 408 along line C-C shows the distance 436.

Figure 5:
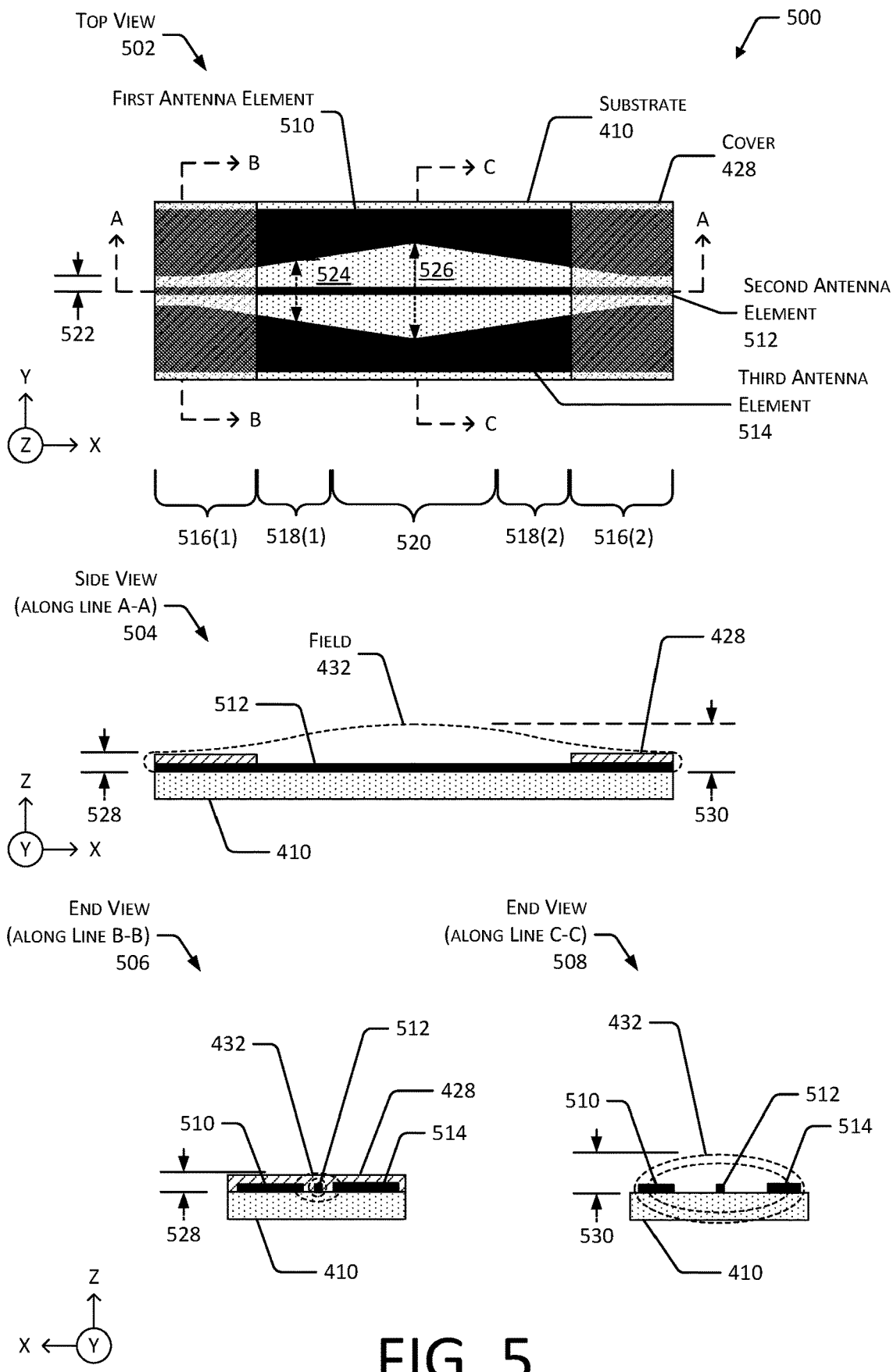
FIG. 5 illustrates a second implementation of the antenna in a planar waveguide configuration.

FIG. 5 illustrates a second implementation 500 of the antenna 112 in a planar waveguide configuration. Depicted are a top view 502, a side view 504 of a cross section along a centerline of the antenna 112, an end view 506 of a first cross section perpendicular to the centerline, and an end view 508 of a second cross section perpendicular to the centerline.

The antenna 112 comprises a substrate 410. A first antenna element 510, a second antenna element 512, and a third antenna element 514 may be affixed to a first surface of the substrate 410. The antenna elements may comprise a wire, trace, or other electrically conductive material. For example, the transmitter 118 may have a transmitter output comprising a first output terminal and a second output terminal. The first output terminal may comprise a signal line while the second output terminal may comprise a ground line associated with an amplifier of the transmitter 118. The first output terminal may be connected to the second antenna element 512 at a first end of the antenna 112 while the second output terminal may be connected to one or more of the first antenna element 510 or the third antenna element 514 at the first end of the antenna 112.

The second antenna element 512 extends along a centerline of the antenna 112. The first antenna element 510 and the third antenna element 514 mirror one another, on opposite sides of the second antenna element 512. For example, a first point on an inner edge of the first antenna element 510 and a second point on an inner edge of the third antenna element 514 are at substantially equal distances from the centerline 112, wherein a line extending through the first point and the second point is perpendicular to the centerline. A first distance and a second distance may be deemed substantially equal if they are within a threshold value of one another. The threshold value may be determined based on manufacturing processes, tolerances associated with design of the antenna, and so forth.

A geometry or relative arrangement of the antenna elements may be described in terms of three sections. While the geometry depicted here is symmetrical with respect to two axes, asymmetrical designs are also possible, such as described below with regard to FIG. 7.

For ease of discussion, and not necessarily as a limitation, the antenna 112 is shown divided into a pair of first sections 516(1) and 516(2), a pair of second sections 518(1) and 518(2), and a third section 520. The first section 516(1) is proximate to a first end of the antenna 112 while the first section 516(2) is proximate to a second end of the antenna 112. The second section 518(1) is adjacent to the first section 516(1) and the second section 518(2) is adjacent to the first section 516(2). The third section 520 is between the second section 518(1) and the second section 518(2).

Proximate to the first end of the antenna 112, the first antenna element 510 and the second antenna element 512 are separated from one another by a distance 522. For example, a first point on the first antenna element 510 and a second point on the second antenna element 512 that are both a first distance from the first end of the antenna 112 may be separated by the distance 522. Outermost edges, farthest from the second antenna element 512, of the first antenna element 510 and the third antenna element 514 may be parallel to the second antenna element 512. In contrast, at least a portion of the innermost edges of the first antenna element 510 and the third antenna element 514 are not parallel to the second antenna element 512.

The first section 516 may include the terminals, contacts, or other structure to which other circuitry is attached to the antenna elements. The first section 516 may exhibit a first impedance at a specified frequency. For example, the first section 516 may exhibit an impedance that matches an impedance of the RF transceiver 114 at a frequency used by the RF transceiver 114.

As the distance from the first end increases, the spacing between the innermost edges of first antenna element 510 and the second antenna element 512 increases. For example, within the second section 518(1) that is a second distance from the first end of the antenna 112, the first antenna element 510 and the second antenna element 512 are a second distance 524 apart. The second distance 524 is greater than the first distance 522.

The antenna elements are separated with a geometry that avoids discontinuities such as two straight line sections meeting at a vertex. Instead, the antenna elements gradually separate and merge due to the curvature of the antenna elements. By avoiding discontinuities, the antenna 112 avoids an abrupt change in impedance which would introduce reflections of the signals on the antenna 112.

Within the third section 520 that is shown here centered on a midpoint between the first end and the second end, the first antenna element 510 and the second antenna element 512 are a third distance 526 apart. The third distance 526 is greater than the second distance 524. The impedance in the third section 520 differs from the impedance in the first section 516. Due to the third distance 526 being greater than the first distance 522, the fringe effect of the electric field associated with the signal 108 in the antenna 112 is increased, as shown below, resulting in an increased sample depth for the signal 108.

In some implementations a cover 428 may be used that is adjacent to the antenna elements and is between the antenna elements and the user 102. The cover 428 may comprise a non-conductive material. For example, the cover 428 may comprise plastic, glass, and so forth. The cover 428 may be transparent to the signal(s) 108.

In the implementation depicted, the cover 428 is arranged atop the first sections 516(1) and 516(2) while the portion of the first antenna element 510 and the second antenna element 512 in the second sections 518(1) and 518(2) and the third section 520 may come into direct contact with the skin of the user 102. In other implementations the cover 428 may cover all sections of the antenna 112 or may be omitted.

As described above, the antenna elements may comprise a biocompatible material such as gold, silver, rhodium, and so forth. In addition to being used to emit and acquire the signal 108, in implementations where the antenna elements are in contact with the user 102, they may be used to acquire other information.

The antenna elements may be on, affixed to, incorporated within, or otherwise maintained by the substrate 410. The substrate 410 may be rigid or flexible. For example, the substrate 410 may comprise a plastic layer upon which the antenna elements have been deposited, printed, adhered, and so forth. In one implementation the antenna 112 may comprise a flexible printed circuit with the antenna elements comprising traces thereon.

One or more apertures 430 or sensors 142 (not shown here) may be located between or near the antenna elements of the antenna 112.

The side view 504 depicts a cross section of the antenna 112 along a centerline indicated by line A-A. Shown in this view is a representation of an electric field 432 associated with a signal 108. In the first sections 516(1) and 516(2) the field 432 extends a distance 528 from the substrate 410. In the third section 520 the field 432 extends a distance 530 from the substrate 410, where distance 530 is greater than distance 528. During use, the antenna 112 is placed proximate to the user 102 such that the field 432 impinges on at least a portion of the user 102.

The end view 506 along line B-B also shows the distance 528 while the end view 508 along line C-C shows the distance 530. Also depicted in this illustration is that the first antenna element 510, the second antenna element 512, and the third antenna element 514 are located in a common plane, that is they are coplanar with one another.

Figure 6:
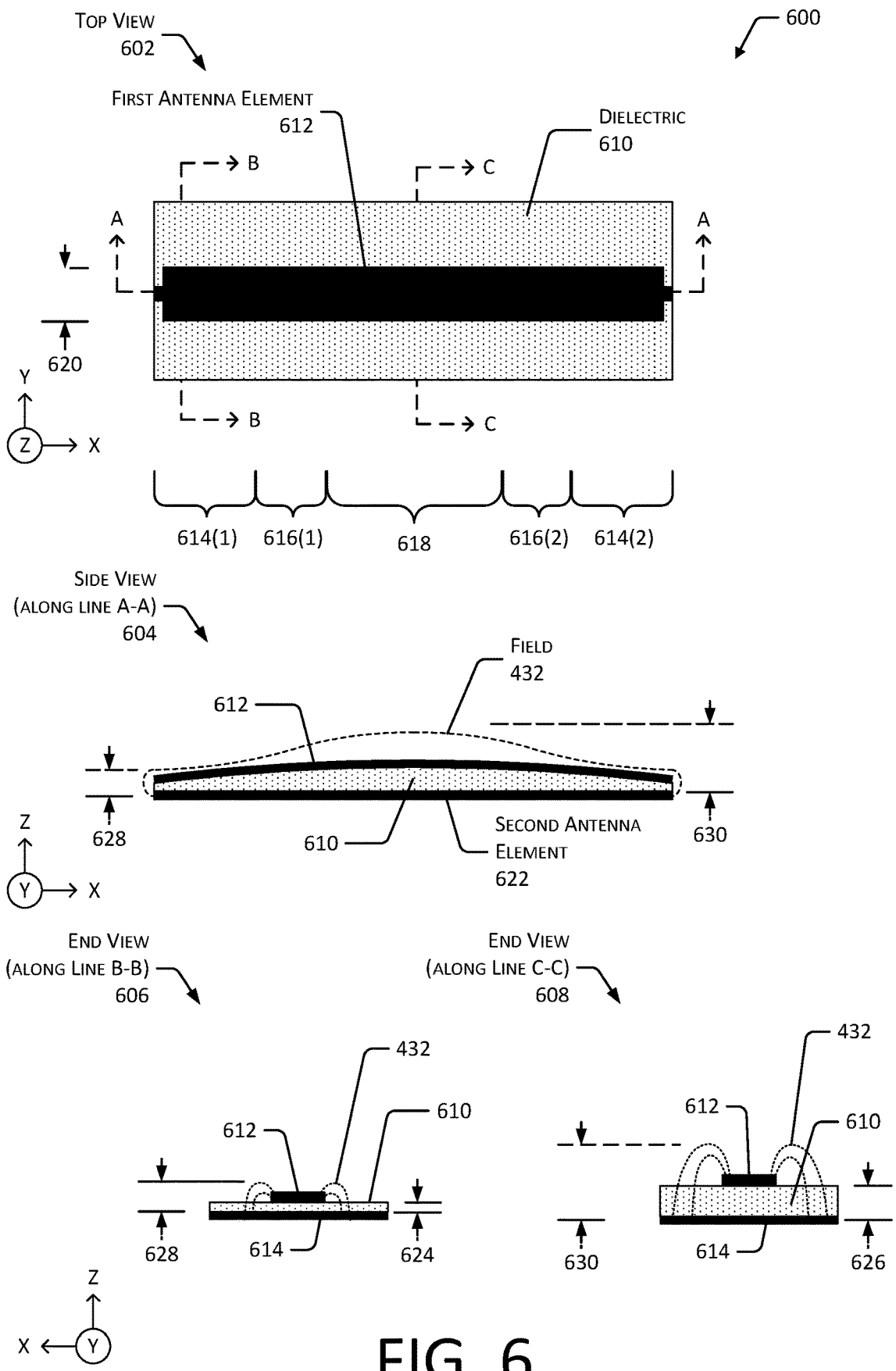
FIG. 6 illustrates a third implementation of the antenna in a microstrip configuration.

FIG. 6 illustrates a third implementation 600 of the antenna 112 in a microstrip configuration. Depicted are a top view 602, a side view 604 of a cross section along a centerline of the antenna 112, an end view 606 of a first cross section along line B-B that is perpendicular to the centerline, and an end view 608 of a second cross section along line C-C that is perpendicular to the centerline.

The antenna 112 comprises a dielectric 610. For example, the dielectric 610 may comprise a plastic, glass, fiberglass, or other material. The antenna elements may be on, printed onto, deposited, adhered, affixed to, laminated to, incorporated within, or otherwise maintained by the dielectric 610. The antenna elements of the antenna 112 may comprise a wire, trace, or other electrically conductive material. The dielectric 610 may be rigid or flexible. In some implementations the dielectric 610 may comprise a substrate.

A first antenna element 612 is shown affixed to a first surface of the dielectric 610. The first antenna element 612 extends along a centerline of the antenna 112.

As described above, the geometry or relative arrangement of the antenna elements may be described in terms of three sections. While the geometry depicted here is symmetrical with respect to two axes, asymmetrical designs are also possible, such as described below with regard to FIG. 7.

For ease of discussion, and not necessarily as a limitation, the antenna 112 is shown divided into a pair of first sections 614(1) and 614(2), a pair of second sections 616(1) and 616(2), and a third section 618. The first section 614(1) is proximate to a first end of the antenna 112 while the first section 614(2) is proximate to a second end of the antenna 112. The second section 616(1) is adjacent to the first section 614(1) and the second section 616(2) is adjacent to the first section 614(2). The third section 618 is between the second section 616(1) and the second section 616(2).

The first antenna element 612 has a first width 620 and may include the terminals, contacts, or other structure to which other circuitry is attached to the antenna elements.

The side view 604 depicts a cross section of the antenna 112 along a centerline indicated by line A-A. A second antenna element 622 is shown affixed to a second surface of the substrate 410. The second surface is on a side opposite the first surface. The second antenna element 622 also extends along a centerline of the antenna 112 and is wider than the first width 620.

As the distance from the first end increases, the thickness of the dielectric 610 varies. The end view 606 at the first end of the antenna 112 shows the dielectric 610 with a first thickness 624. Towards a midpoint of the antenna 112 as shown in the end view 608, the dielectric 610 has a second thickness 626 that is greater than the first thickness 624.

Shown in this view is a representation of the electric field 432 associated with a signal 108. In the first sections 614(1) and 614(2) the field 432 extends a distance 628 from the dielectric 610. In the third section 618 the field 432 extends a distance 630 from the dielectric 610, where distance 630 is greater than distance 628. During use, the antenna 112 is placed proximate to the user 102 such that the field 432 impinges on at least a portion of the user 102.

Also shown in the end views 606 and 608 is that the second antenna element 622 is wider than the first antenna element 612.

The first section 614 may exhibit a first impedance at a specified frequency. For example, the first section 614 may exhibit an impedance that matches an impedance of the RF transceiver 114 at a frequency used by the RF transceiver 114.

The antenna elements are separated with a geometry that avoids discontinuities such as two straight line sections meeting at a vertex. Instead, the antenna elements gradually separate and then merge due to the change in thickness of the dielectric 610. By avoiding discontinuities, the antenna 112 avoids an abrupt change in impedance which would introduce reflections of the signals on the antenna 112.

The impedance in the third section 618 differs from the impedance in the first section 614. Due to the second thickness 626 being greater than the first thickness 624, the fringe effect of the electric field associated with the signal 108 in the antenna 112 is increased, as shown below, resulting in an increased sample depth for the signal 108.

In some implementations a cover 428 (not shown) may be used that is adjacent to the antenna elements and is between the antenna elements and the user 102. The cover 428 may comprise a non-conductive material. For example, the cover 428 may comprise plastic, glass, and so forth. The cover 428 may be transparent to the signal(s) 108.

The cover 428 may be arranged atop the first sections 614(1) and 614(2) while the portion of the first antenna element 612 and the second antenna element 622 in the second sections 616(1) and 616(2) and the third section 618 may come into direct contact with the skin of the user 102. In other implementations the cover 428 may cover all sections of the antenna 112 or may be omitted.

As described above, the antenna elements may comprise a biocompatible material such as gold, silver, rhodium, and so forth. In addition to being used to emit and acquire the signal 108, in implementations where the antenna elements are in contact with the user 102, they may be used to acquire other information.

One or more apertures 430 or sensors 142 (not shown here) may be located between or near the antenna elements of the antenna 112. For example, an aperture 430 may extend through the dielectric 610 and the second antenna element 622.

Figure 7:
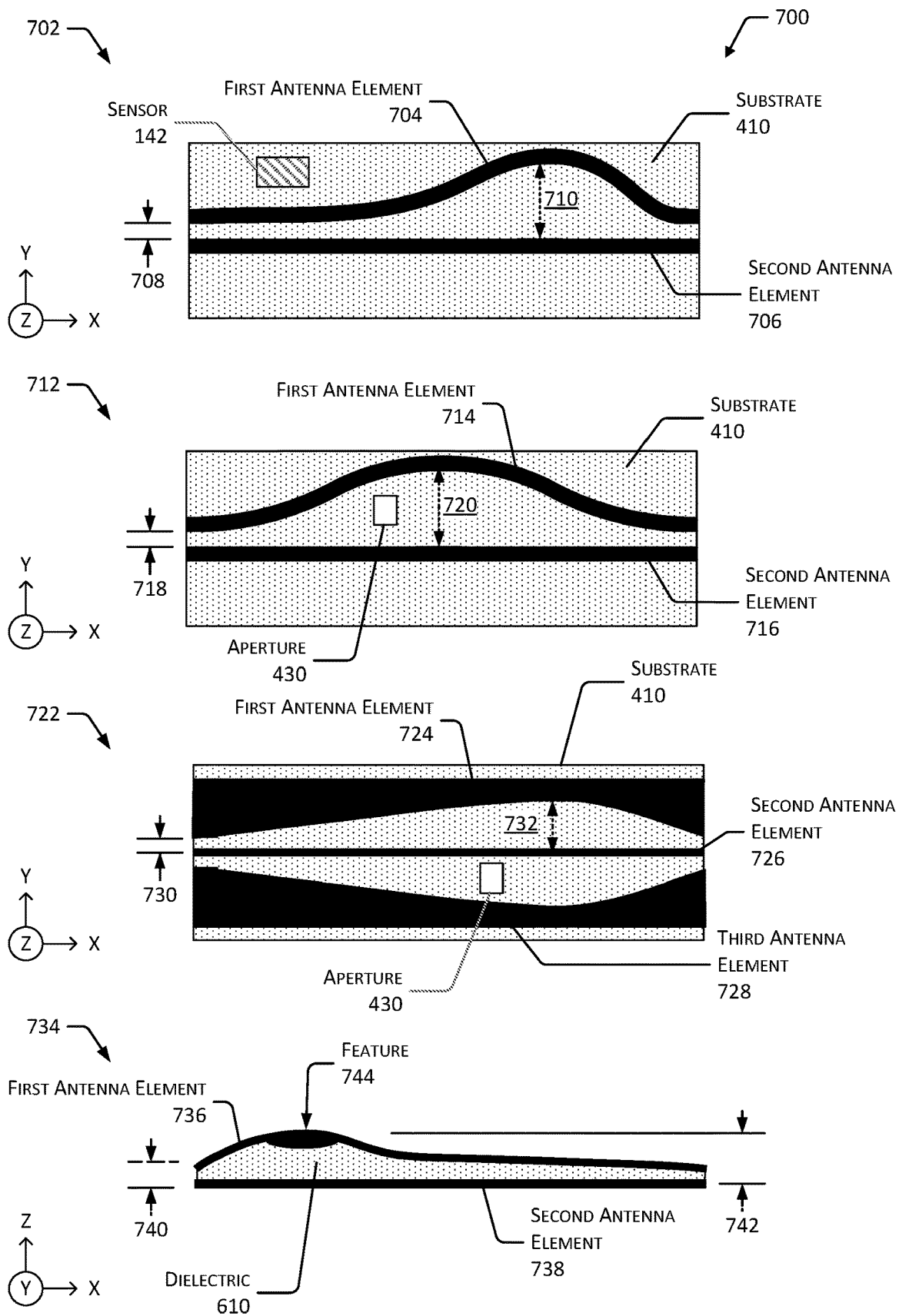
FIG. 7 illustrates various implementations of the antenna.

FIG. 7 illustrates various implementations 700 of the antenna 112. While the antenna elements in the implementations shown in FIGS. 4-6 are symmetrical with respect to at least one axis, asymmetrical geometries may be used.

A first implementation 702 depicts the substrate 410, a first antenna element 704, and a second antenna element 706 on a same surface or side of the substrate 410. At a first end of the antenna 112 in this implementation, the innermost edges of the first antenna element 704 and the second antenna element 706 are a first distance 708 apart. The second antenna element 706 extends in a straight line along a long axis of the antenna 112. In comparison, the first antenna element 704 is arcuate, curving away from the second antenna element 706 until a maximum distance 710 between the innermost edges of the first antenna element 704 and the second antenna element 706 is attained. The point of maximum distance 710 is located closer to the second end of the antenna 112 than the first end of the antenna 112. The first antenna element 704 then curves back towards the second antenna element 706 to being the first distance 708 apart at the second end of the antenna.

The placement of the portion of the antenna 112 with the enhanced fringing due to the maximum distance 710 may take into consideration anatomical features of the user 102. For example, the skin in humans on the ventral (inner)

portion of the wrist is typically thinner than the skin on the dorsal (outer) portion of the wrist. In one implementation the antenna 112 may be incorporated into the support structure 110, such as a wrist band. To improve the detection of particular types of molecules 106, the maximum distance 710 between the antenna elements 704 and 706 may be positioned to be proximate to the ventral portion during wear.

Also shown is a sensor 142 that is also affixed to the substrate 410.

A second implementation 712 depicts the substrate 410, a first antenna element 714, and a second antenna element 716. At a first end of the antenna 112 in this implementation, the innermost edges of the first antenna element 714 and the second antenna element 716 are a first distance 718 apart. The second antenna element 716 extends in a straight line along a long axis of the antenna 112. In comparison, the first antenna element 714 is arcuate, curving away from the second antenna element 716 until a maximum distance 720 between the innermost edges of the first antenna element 714 and the second antenna element 716 is attained. The point of maximum distance 720 is located at or near a midpoint between the first end and the second end of the antenna 112. The first antenna element 714 then curves back towards the second antenna element 716 to being the first distance 718 apart at the second end of the antenna.

An aperture 430 is shown in the substrate 410, located between the first antenna element 714 and the second antenna element 716.

A third implementation 722 depicts the substrate 410, a first antenna element 724, a second antenna element 726, and a third antenna element 728. The second antenna element 726 extends along a centerline of the antenna 112. The first antenna element 724 and the third antenna element 728 mirror one another, on opposite sides of the second antenna element 726.

At a first end of the antenna 112 in this implementation, the innermost edges of the first antenna element 724 and the second antenna element 726 are a first distance 730 apart. The second antenna element 726 extends in a straight line along a long axis of the antenna 112.

Proximate to the first end of the antenna 112, the first antenna element 724 and the second antenna element 726 are separated from one another by a distance 730. For example, a first point on the first antenna element 724 and a second point on the second antenna element 726 that are both a first distance from the first end of the antenna 112 may be separated by the distance 730. Outermost edges, farthest from the second antenna element 726, of the first antenna element 724 and the third antenna element 728 may be parallel to the second antenna element 724. In contrast, at least a portion of the innermost edges of the first antenna element 724 and the third antenna element 728 are not parallel to the second antenna element 726.

As the distance from the first end increases, the spacing between the innermost edges of first antenna element 724 and the second antenna element 726 increases. For example, at a second distance from the first end of the antenna 112, the first antenna element 724 and the second antenna element 726 are a maximum distance 732 apart. The maximum distance 732 is greater than the first distance 730. As shown in this illustration, the point of maximum distance 732 is located between a midpoint of the antenna 112 and the second end of the antenna 112.

A fourth implementation 734 depicts the dielectric 610, a first antenna element 736 on a first side of the dielectric 610 and a second antenna element 738 on a second side of the dielectric 610. The thickness of the dielectric 610 varies from a first thickness 740 at the first end to a second thickness 742 that is greater than the first thickness.

Towards the second end, the thickness of the dielectric 610 then reduces back to the first thickness 740. The bulge in the dielectric 610 to the second thickness 742 may be located between the first end and a midpoint of the antenna 112.

In some implementations the thickness of the antenna elements may change. These changes in thickness may also be gradual, to avoid discontinuities that would reflect power along the antenna elements. For example, a feature 744 comprising a first portion of the first antenna element 736 that is thicker than a second portion of the first antenna element 736 may be provided. In the implementation depicted here, the feature 744 is positioned within the area with the second thickness 742. This feature 744 may further enhance the fringing effect, changing the sample depth. In other implementations, instead of, or in addition to, a change in thickness, one or more antenna elements may exhibit a change in width.

The antennas 112 described in this disclosure may be used in various configurations. In one implementation, the antenna 112 may be used in a double-ended or through mode, with the transmitter 118 connected to the antenna elements on the first end of the antenna 112 and the receiver 120 connected to the antenna elements on the second end.

In another configuration, the antenna 112 may be used in a single-ended mode in which a device such as the transmitter 118 or the receiver 120 is attached to the antenna elements on the first end and an electrical resistance is placed across the antenna elements on the second end. For example, a 50 ohm resistor may have a first terminal and a second terminal. The first terminal may be connected to an end of the first antenna element proximate to the second end of the antenna 112 while the second terminal is connected to the end of the second antenna element proximate to the second end of the antenna 112. In other implementations the resistor may comprise a feature, such as a printed resistor pattern placed on the substrate 410 or the dielectric 610.

In some implementations the opposite ends of the antenna 112 may have different impedances. For example, the terminals of the antenna 112 at the first end may be separated by a first distance and have a first impedance at a given frequency while the terminals at the second end may be separated by a second distance greater than the first distance and have a second impedance at the given frequency that differs from the first. A resistance that corresponds to the impedance may be placed across the terminals at the second end. For example, the antenna 112 may experience 50 ohms of impedance at the given frequency across the terminals at the first end and 1000 ohms of impedance at the given frequency across the terminals at the second end. A resistance of 1000 ohms may connect the terminals at the second end.

The transmitter 118 may have a transmitter output comprising a first output terminal and a second output terminal. For example, the first output terminal may comprise a signal line while the second output terminal may comprise a ground line associated with an amplifier of the transmitter 118. The first output terminal may be connected to the first antenna element at a first end of the antenna 112 while the second output terminal may be connected to the second antenna element at the first end of the antenna 112.

The receiver 120 may have a receiver input that comprises a first input terminal and a second input terminal. For example, the first input terminal may comprise a signal line while the second input terminal may comprise a ground line. In the double-ended mode, the first input terminal may be connected to the first antenna element at a second end of the antenna 112 while the second input terminal may be connected to the second antenna element at the second end of the antenna 112.

In other implementations other arrangements of electrical conductors and insulators may be used to produce the antenna 112. For example, in the implementations depicted at 500, 702, 712, 722 and so forth, the arrangement of electrical conductors and substrate or dielectric may be inverted. Continuing the example, in the implementation of 722 the shaded area(s) indicated as substrate 410 may instead be electrical conductors acting as antenna elements while the dark areas indicated as antenna elements may instead be the substrate or a dielectric.

Figure 8:
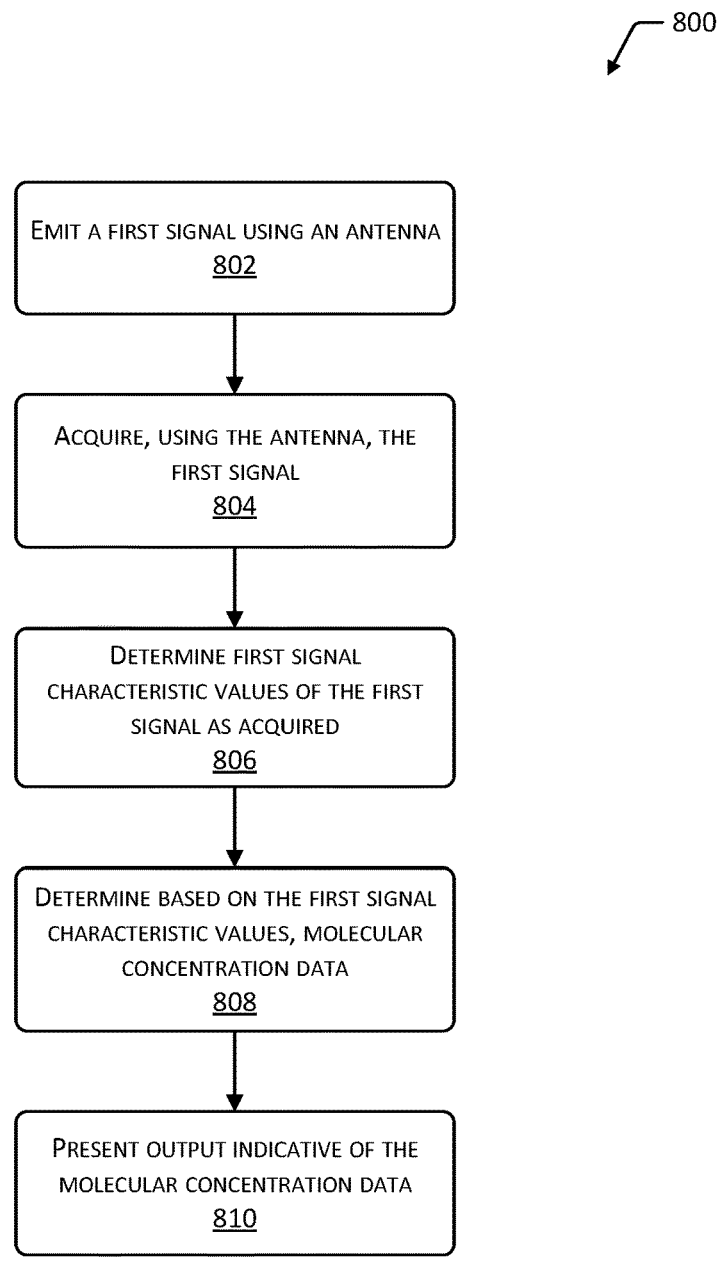
FIG. 8 illustrates a flow diagram of a process of using radio frequency signals emitted and acquired by the antenna to determine molecular concentration data, according to one implementation.

FIG. 8 illustrates a flow diagram 800 of a process of using radio frequency signals 108 emitted and acquired by one or more antennas 112 to determine molecular concentration data 140, according to one implementation. The process may be implemented at least in part by the wearable device 104.

At 802 a first signal 108 is emitted using the first antenna 112. For example, the transmitter 118 may generate the signal 108 which is provided to the first antenna 112(1) which emits or radiates the signal 108 towards the user 102.

At 804, the first signal is acquired using the first antenna 112(1) or another antenna 112(N). In some implementations, the first signal may be acquired using an antenna 112 not connected to the transmitter 118. For example, the first signal 108 may be emitted by the first antenna 112(1) and be acquired by a second antenna 112(2). In other implementations one or more directional couplers, duplexers, or other devices may be used to transmit and acquire the first signal using the first antenna 112(1).

At 806 first signal characteristic values 128 of the first signal as acquired are determined. For example, the signal characteristic values 128 may include frequency data 130, phase data 132, amplitude data 134, and so forth.

At 808, based on the first signal characteristic values 128, molecular concentration data 140 is determined. For example, the first signal characteristics values 128 may be used as input to the molecular reference data 138 to determine a corresponding concentration of a particular type of molecule 106. In another example the first signal characteristic value(s) 128 may be provided as input to a machine learning system which then provides as output the molecular concentration data 140.

At 810 output indicative of the molecular concentration data 140 is presented. In one implementation, the user interface module 144 may generate output data 146 that is used by the one or more output devices 148 to present output to the user 102. For example, a graphical indication may be provided using a display device 148(3) of the other device 150.

In some implementations a sample depth may be determined. For example, the sample depth may be determined based on a type of molecule 106 that is being measured, data from one or more of the other sensors 142, and so forth. For example, the sample depth may be determined based on sensor output from the temperature sensor 142(6). A first sample depth may be determined if the user's 102 temperature is within a first range of temperatures while a second sample depth may be determined if the user's 102 temperature is within a second range of temperatures. In another example, the sample depth may be determined based on the amplitude and duration of motion as indicated by the accelerometer 142(10). For example, if amplitude and duration of motion is less than a first threshold value, a first sample depth may be determined. If the amplitude and duration of motion is greater than the first threshold value, a second sample depth may be determined. In still another example, the sample depth may be provided based on information about the user 102. For example, the sample depth may be determined based on the diameter of the user's 102 wrist.

Based on the first sample depth, a determination is made as to which of the one or more of the antennas 112 to use. For example, the first antenna 112(1) may have provide the first sample depth, while the second antenna 112(2) provides a second sample depth, while a third antenna 112(3) provides a third sample depth, and so forth. In another example, two or more antennas 112 may be used that are separated by some distance to produce a desired sample depth. For example, the first antenna 112(1) may be connected to the transmitter 118 while the second antenna 112(2) is connected to the receiver 120. The increased distance between the two antennas may provide an increased sample depth. The switching circuitry or other circuitry in the wearable device 104 may be operated to provide a particular combination of antennas 112.

The antenna 112 may be implemented in various combinations of the implementations described. For example, one combination may comprise a first, second, and third antenna element. The first antenna element and the second antenna element may be arranged on a first side of a dielectric 610 with a variable spacing between the two elements, such as depicted in the top view 402 in FIG. 4. The third antenna element may be arranged on a second side of the dielectric 610 that is opposite the first side. The thickness in the dielectric 610 may vary, as depicted in the side view 604 in FIG. 6. Other combinations are also possible.

While the system and techniques described herein are used with respect to measure humans, it is understood that these techniques may be used to monitor other types of animals. In some implementations, the systems and techniques may be used to characterize other objects. For example, the system may be used to determine a sugar concentration in a fruit, water concentration in a mixture, and so forth.

The processes discussed herein may be implemented in hardware, software, or a combination thereof. In the context of software, the described operations represent computer-executable instructions stored on one or more non-transitory computer-readable storage media that, when executed by one or more processors, perform the recited operations. Generally, computer-executable instructions include routines, programs, objects, components, data structures, and the like that perform particular functions or implement particular abstract data types. Those having ordinary skill in the art will readily recognize that certain steps or operations illustrated in the figures above may be eliminated, combined, or performed in an alternate order. Any steps or operations may be performed serially or in parallel. Furthermore, the order in which the operations are described is not intended to be construed as a limitation.

Embodiments may be provided as a software program or computer program product including a non-transitory computer-readable storage medium having stored thereon instructions (in compressed or uncompressed form) that may be used to program a computer (or other electronic device) to perform processes or methods described herein. The computer-readable storage medium may be one or more of an electronic storage medium, a magnetic storage medium, an optical storage medium, a quantum storage medium, and so forth. For example, the computer-readable storage media may include, but is not limited to, hard drives, optical disks, read-only memories (ROMs), random access memories (RAMs), erasable programmable ROMs (EPROMs), electrically erasable programmable ROMs (EEPROMs), flash memory, magnetic or optical cards, solid-state memory devices, or other types of physical media suitable for storing electronic instructions. Further, embodiments may also be provided as a computer program product including a transitory machine-readable signal (in compressed or uncompressed form). Examples of transitory machine-readable signals, whether modulated using a carrier or unmodulated, include, but are not limited to, signals that a computer system or machine hosting or running a computer program can be configured to access, including signals transferred by one or more networks. For example, the transitory machine-readable signal may comprise transmission of software by the Internet.

Separate instances of these programs can be executed on or distributed across any number of separate computer systems. Thus, although certain steps have been described as being performed by certain devices, software programs, processes, or entities, this need not be the case, and a variety of alternative implementations will be understood by those having ordinary skill in the art.

Additionally, those having ordinary skill in the art will readily recognize that the techniques described above can be utilized in a variety of devices, environments, and situations. Although the subject matter has been described in language specific to structural features or methodological acts, it is to be understood that the subject matter defined in the appended claims is not necessarily limited to the specific features or acts described. Rather, the specific features and acts are disclosed as illustrative forms of implementing the claims.

What is claimed is:

1. A wearable device comprising:
   a support structure that retains the wearable device proximate to a user;
   an antenna mounted to the support structure, the antenna comprising:
      a first portion of the antenna that is affixed to a substrate, wherein the first portion of the antenna has a first end, a first midpoint, and a second end, and
      a second portion of the antenna that is affixed to the substrate, wherein the second portion of the antenna has a third end that is a first distance from the first end, a second midpoint that is a second distance from the first midpoint, and a fourth end that is the first distance from the second end, and further wherein the second distance is greater than the first distance;
   a transmitter connected to the first end of the first portion of the antenna and the third end of the second portion of the antenna;
   a receiver connected to the second end of the first portion of the antenna and the fourth end of the second portion of the antenna;
   a first memory, storing computer-executable instructions; and
   a first hardware processor, wherein the first hardware processor executes the computer-executable instructions to:
      operate the transmitter to generate a first signal at a first time;
      operate the receiver at the first time to receive the first signal;
      determine a first phase difference of the first signal as received by the receiver relative to the first signal generated by the transmitter; and
      determine, using the first phase difference, a concentration of a type of molecule.

2. The wearable device of claim 1, further comprising:
   a first non-conductive cover that is adjacent to the first end of the first portion of the antenna and adjacent to the third end of the second portion of the antenna, wherein the first non-conductive cover is between the antenna and the user during use;
   a second non-conductive cover that is adjacent to the second end of the first portion of the antenna and adjacent to the fourth end of the second portion of the antenna, wherein the second non-conductive cover is between the antenna and the user during use; and
   an uncovered area between the first non-conductive cover and the second non-conductive cover, wherein the first portion of the antenna and the second portion of the antenna are exposed within the uncovered area.

3. A device comprising:
   a first portion of an antenna on a substrate, wherein the first portion of the antenna comprises:
      a first end,
      a second end,
      a first point at a first distance from the first end,
      a second point at a second distance from the first end, and
      a third point at a third distance from the first end;
   a second portion of the antenna on the substrate, wherein the second portion of the antenna comprises:
      a third end,
      a fourth end,
      a fourth point at a fourth distance from the third end,
      a fifth point at a fifth distance from the third end, and
      a sixth point at a sixth distance from the third end;
   a transmitter having a transmitter output connected to the first portion of the antenna and to the second portion of the antenna;
   a receiver having a receiver input connected to the first portion of the antenna and to the second portion of the antenna;
   a first memory, storing computer-executable instructions; and
   a first hardware processor, wherein the first hardware processor executes the computer-executable instructions to:
      operate the transmitter to generate one or more signals;
      operate the receiver to receive the one or more signals; and
      determine one or more signal characteristic values of the one or more signals as received by the receiver.

4. The device of claim 3, wherein:
   at least a portion of the first portion of the antenna is not parallel to the second portion of the antenna.

5. The device of claim 3, wherein the first portion of the antenna is on a first side of the substrate and the second portion of the antenna is on a second side of the substrate.

6. The device of claim 3, wherein:
   the first portion of the antenna is on a first side of the substrate,
   the second portion of the antenna is on a second side of the substrate opposite the first side,
   the first point is aligned with the fourth point,
   the substrate has a first thickness between the first point and the fourth point, the second point is aligned with the fifth point,
the substrate has a second thickness between the second point and the fifth point,
the first thickness is less than the second thickness,
the third point is aligned with the sixth point,
the substrate has a third thickness between the third point and the sixth point, and
the second thickness is greater than the third thickness.

7. The device of claim 3, wherein:
the first point is a seventh distance from a centerline of the substrate,
the fourth point is the seventh distance from the centerline,
the first distance and the fourth distance are substantially equal,
the second point is an eighth distance from the centerline,
the fifth point is the eighth distance from the centerline,
the second distance and the fifth distance are substantially equal,
the third point is a ninth distance from the centerline,
the sixth point is the ninth distance from the centerline, and
the third distance and the sixth distance are substantially equal.

8. The device of claim 3, wherein:
the first point is a seventh distance from a centerline of the substrate,
the fourth point is the seventh distance from the centerline,
the second point is an eighth distance from the centerline,
the fifth point is the eighth distance from the centerline,
the third point is a ninth distance from the centerline, and
the sixth point is the ninth distance from the centerline.

9. The device of claim 3, wherein:
the first point is a seventh distance from the fourth point,
the second point is an eighth distance from the fifth point,
the seventh distance is not equal to the eighth distance,
the third point is a ninth distance from the sixth point, and
the eighth distance is not equal to the ninth distance.

10. The device of claim 3, wherein:
a first impedance at a first frequency is measured between the first end and the third end,
a second impedance at the first frequency is measured between the second point and the fifth point, and
a third impedance at the first frequency is measured between the second end and the fourth end.

11. The device of claim 3, wherein:
the transmitter output comprises a first output terminal and a second output terminal,
the first output terminal is connected to the first end,
the second output terminal is connected to the third end,
the receiver input comprises a first input terminal and a second input terminal,
the second end is connected to the first input terminal, and
the fourth end is connected to the second input terminal.

12. The device of claim 3, further comprising:
a resistor having a first terminal and a second terminal, wherein:
the first terminal is connected to the second end, and
the second terminal is connected to the fourth end.

13. A device comprising:
a first portion of an antenna on a substrate, wherein the first portion of the antenna comprises:
a first end,
a second end,
a first point at a first distance from the first end,
a second point at a second distance from the first end, and
a third point at a third distance from the first end; and
a second portion of the antenna on the substrate, wherein the second portion of the antenna comprises:
a third end,
a fourth end,
a fourth point at a fourth distance from the third end,
a fifth point at a fifth distance from the third end, and
a sixth point at a sixth distance from the third end,
wherein:
a first section of the first portion of the antenna that is adjacent to a second section of the second portion of the antenna is not parallel to the second section.

14. The device of claim 13, wherein the first portion of the antenna is on a first side of the substrate and the second portion of the antenna is on a second side of the substrate.

15. The device of claim 13, wherein:
the first portion of the antenna is on a first side of the substrate,
the second portion of the antenna is on a second side of the substrate opposite the first side,
the substrate has a first thickness between the first point and the fourth point,
the substrate has a second thickness between the second point and the fifth point,
the first thickness is less than the second thickness,
the substrate has a third thickness between the third point and the sixth point, and
the second thickness is greater than the third thickness.

16. The device of claim 13, wherein:
the first point is a seventh distance from a centerline,
the fourth point is the seventh distance from the centerline,
the first distance and the fourth distance are substantially equal,
the second point is an eighth distance from the centerline,
the fifth point is the eighth distance from the centerline,
the second distance and the fifth distance are substantially equal,
the third point is a ninth distance from the centerline,
the sixth point is the ninth distance from the centerline, and
the third distance and the sixth distance are substantially equal.

17. The device of claim 13, wherein:
the first point is a seventh distance from a centerline,
the fourth point is the seventh distance from the centerline,
the second point is an eighth distance from the centerline,
the fifth point is the eighth distance from the centerline,
the third point is a ninth distance from the centerline, and
the sixth point is the ninth distance from the centerline.

18. The device of claim 13, wherein:
the first point is a seventh distance from the fourth point,
the second point is an eighth distance from the fifth point,
the seventh distance is not equal to the eighth distance,
the third point is a ninth distance from the sixth point, and
the eighth distance is not equal to the ninth distance.

19. The device of claim 13, wherein:
a first impedance at a first frequency is measured between the first end and the third end,
a second impedance at the first frequency is measured between the second point and the fifth point, and
a third impedance at the first frequency is measured between the second end and the fourth end.

20. The device of claim 13, further comprising:
a resistor connecting the second end and the fourth end;
a transmitter having a first output terminal connected to the first end and a second output terminal connected to the third end;
a receiver having a first input terminal connected to the second end and a second input terminal connected to the fourth end;
a first memory, storing computer-executable instructions; and
a first hardware processor, wherein the first hardware processor executes the computer-executable instructions to:
   operate the transmitter to generate one or more signals;
   operate the receiver to receive the one or more signals; and
   determine one or more signal characteristic values of the one or more signals as received by the receiver.

* * * * *